(12) United States Patent
Cai et al.

(10) Patent No.: US 12,171,835 B2
(45) Date of Patent: Dec. 24, 2024

(54) FURAN-ASPIDOSPERMINE DIMER OR PHARMACEUTICALLY ACCEPTABLE SALT THEREOF, AND PREPARATION METHOD, USE AND PHARMACEUTICAL COMPOSITION

(71) Applicant: Kunming Inst. of Botany, Chinese Acad. of Sciences, Kunming (CN)

(72) Inventors: Xianghai Cai, Kunming (CN); Guisheng Zhong, Kunming (CN); Simeng Zhao, Kunming (CN); Meifen Bao, Kunming (CN); Yang Yu, Kunming (CN)

(73) Assignees: Kunming Institute of Botany, Kunming (CN); Chinese Academy of Sciences, Beijing (CN)

( * ) Notice: Subject to any disclaimer, the term of this patent is extended or adjusted under 35 U.S.C. 154(b) by 0 days.

(21) Appl. No.: 17/693,329

(22) Filed: Mar. 12, 2022

(65) Prior Publication Data

US 2022/0296724 A1     Sep. 22, 2022

(30) Foreign Application Priority Data

Mar. 13, 2021   (CN) .......................... 202110270901.2

(51) Int. Cl.
*A61K 47/55*   (2017.01)
*A61K 47/54*   (2017.01)

(52) U.S. Cl.
CPC ............ *A61K 47/55* (2017.08); *A61K 47/545* (2017.08)

(58) Field of Classification Search
CPC .................................................... A61K 47/55
See application file for complete search history.

(56) References Cited

FOREIGN PATENT DOCUMENTS

CN           107011352       *    8/2017

OTHER PUBLICATIONS

Kam, Journal of Natural Products, vol. 56, No. 11, pp. 1865-1871, Nov. 1995.*
Umezawa Biomedicine & Pharmacotherapy (2003), 57(8), 341-350.*
Han-ya. Angewandte Chemie, International Edition (2011), 50(21), 4884-4887.*
Umezawa Biomedicine & Pharmacotherapy 57 (2003) 341-350.*

* cited by examiner

*Primary Examiner* — Nizal S Chandrakumar
(74) *Attorney, Agent, or Firm* — HoustonHogle LLP

(57) ABSTRACT

The present disclosure relates to the technical field of medicine, in particular to a furan-aspidospermine dimer or a pharmaceutically acceptable salt thereof, and a preparation method, use and a pharmaceutical composition. In the present disclosure, the furan-aspidospermine dimer or a pharmaceutically acceptable salt thereof can activate an immune response by increasing a proportion of T lymphocytes and enhance a function of the immune response.

3 Claims, 4 Drawing Sheets

FURAN-ASPIDOSPERMINE DIMER OR PHARMACEUTICALLY ACCEPTABLE SALT THEREOF, AND PREPARATION METHOD, USE AND PHARMACEUTICAL COMPOSITION

CROSS REFERENCE TO RELATED APPLICATION

This patent application claims the benefit and priority of Chinese Patent Application No. 202110270901.2, filed on Mar. 13, 2021, the disclosure of which is incorporated by reference herein in its entirety as part of the present application.

TECHNICAL FIELD

The present disclosure relates to the technical field of medicine, in particular to a furan-aspidospermine dimer or a pharmaceutically acceptable salt thereof, and a preparation method, use and a pharmaceutical composition.

BACKGROUND ART

Diseases caused by immunodeficiency or insufficiency such as tumors and AIDS, or other infectious diseases caused by pathogenic microorganisms, are a worldwide problem, resulting in millions of deaths in China annually. Chemotherapy, antiviral drugs and antibiotics currently used in clinic have certain curative effects, making the active pharmaceutical ingredients act directly on lesions. However, due to a high toxicity and strong drug resistance, these methods will bring huge physical pain and mental stress to the patients. Moreover, most of these diseases cause protective barriers of the body to be broken due to decreased immunity or a deficiency of the immune system. Improving and maintaining the body immunity can treat and prevent these diseases to a large extent, which is also a natural disease resistance instinct of the body. Immune cells are main weapons of the body immune system, and T lymphocytes are main components of the immune cells, with phagocytosis of extraneous invaders as a main function. Therefore, it is a key point in treatment and prevention of the immune diseases by increasing a proportion of the T lymphocytes in the body as well as enhancing their functions.

SUMMARY

An objective of the present disclosure is to provide a furan-aspidospermine dimer or a pharmaceutically acceptable salt thereof, and a preparation method, use and a pharmaceutical composition. The furan-aspidospermine dimer or the pharmaceutically acceptable salt thereof can activate an immune response by increasing a proportion of T lymphocytes as well as enhance a function of the immune response.

To achieve the above objective, the present disclosure provides the following technical solutions:

The present disclosure provides a furan-aspidospermine dimer or a pharmaceutically acceptable salt thereof, having a structure as shown in formula I:

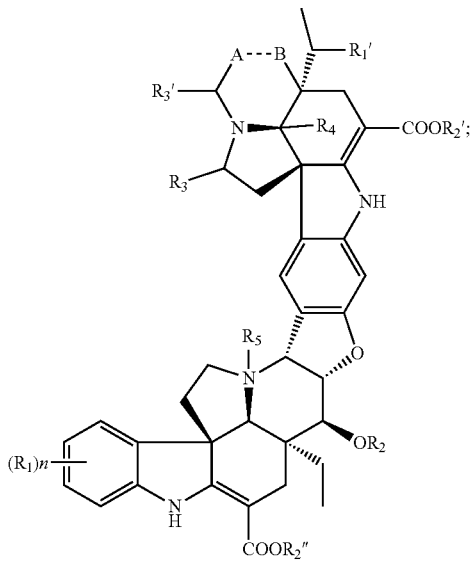

formula I where

R$_1$ and R$_1$' each are independently selected from the group consisting of hydrogen, hydroxyl or C$_{1-6}$ alkoxy; n is a positive integer ranging from 0 to 4;

R$_2$, R$_2$' and R$_2$" each are independently selected from the group consisting of hydrogen or C$_{1-6}$ alkyl; R$_3$ and R$_3$' each are independently selected from the group consisting of hydrogen, hydroxyl and =O;

R$_4$ is selected from the group consisting of hydrogen or hydroxyl; R$_5$ is has no substituent or is =O;

A-B is selected from the group consisting of —CH$_2$—CH$_2$—, —CH=CH—, —HOCH—CHOH—, —CH$_2$—CHOH— or

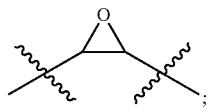

;

and the pharmaceutically acceptable salt thereof is selected from the group consisting of an organic salt or an inorganic salt substituted at positions R$_2$' and R$_2$".

Preferably, when A-B is

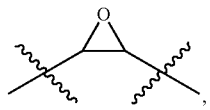 [SMILES: *C1OC1*]

, the furan-aspidospermine dimer or the pharmaceutically acceptable salt thereof may have a structure as shown in formula I-1 to formula I-4:

formula I-1

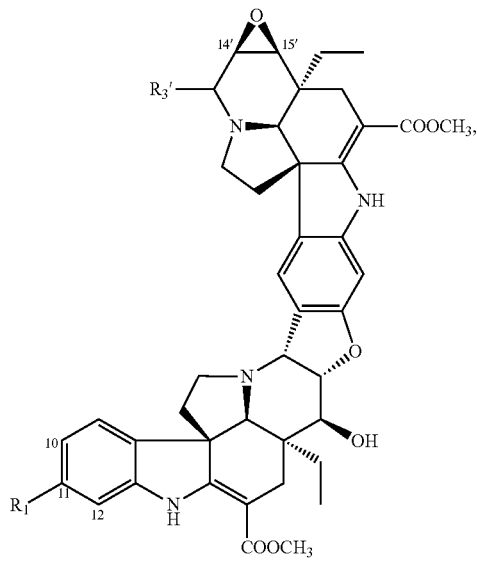

where, $R_1$ is hydrogen, and $R_3'$ is hydrogen; alternatively, $R_1$ is methoxy, and $R_3'$ is hydrogen; alternatively, $R_1$ is hydrogen, and $R_3'$ is =O;

formula I-2

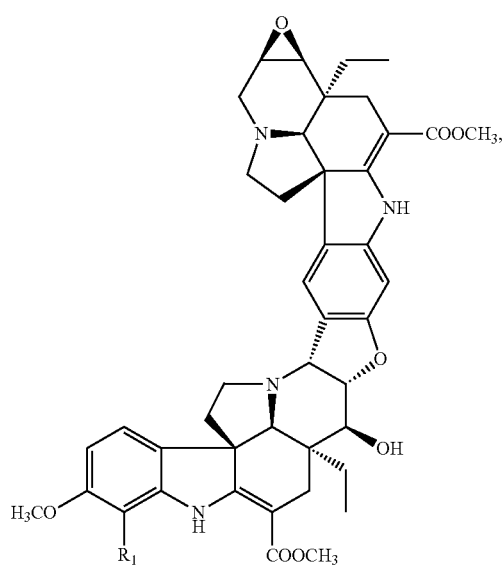

where, $R_1$ is selected from the group consisting of hydroxyl and methoxy;

formula I-3 where, $R_1$ is hydrogen, and $R_5$ has no substituent; alternatively, $R_1$ is methoxy, and $R_5$ has no substituent; alternatively, $R_1$ is methoxy, and $R_5$ is =O; and formula I-4 where, $R_1$ is OH and $R_1'$ is H (denoted as a compound 5); or $R_1$ is H and $R_1'$ is hydroxyl (denoted as a compound 6); or $R_1$ is OH and $R_1'$ is methoxy (denoted as a compound 7).

Preferably, when A-B is —CH$_2$—CHOH—, there may be a β-OH located at position B in —CH$_2$—CHOH—; and the furan-aspidospermine dimer or the pharmaceutically acceptable salt thereof may have a structure as shown in formula I-5:

formula I-5

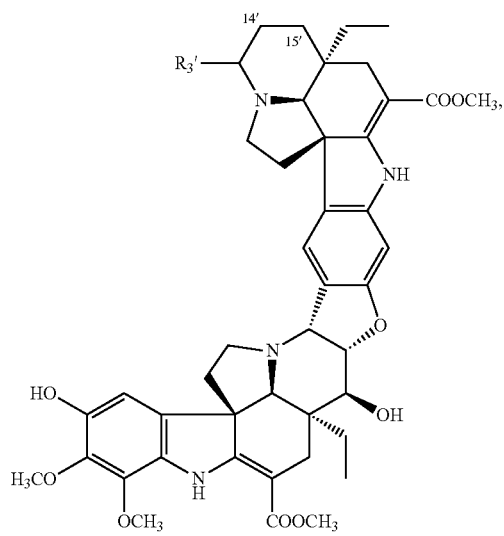

where, $R_3'$ is =O;

when A-B is —HOCH—CHOH—, there may be α-OH located at position A and the β-OH located at position B in —HOCH—CHOH—; and the furan-aspidospermine dimer or the pharmaceutically acceptable salt thereof may have a structure as shown in formula I-5:

formula I-5

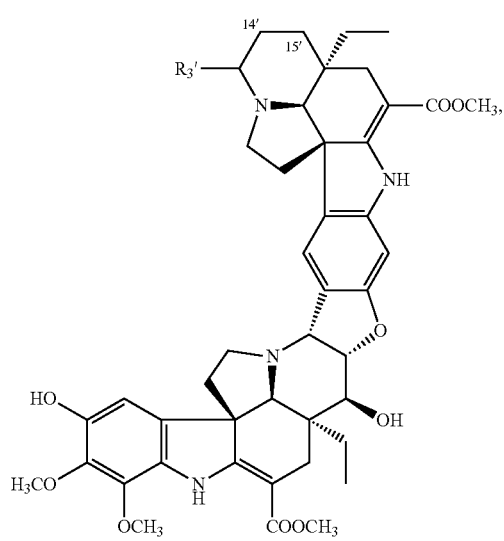

where, $R_3'$ is hydrogen.

Preferably, when A-B is —CH=CH—, the furan-aspidospermine dimer or the pharmaceutically acceptable salt thereof may have a structure as shown in formula I-6 to formula I-9:

formula I-6

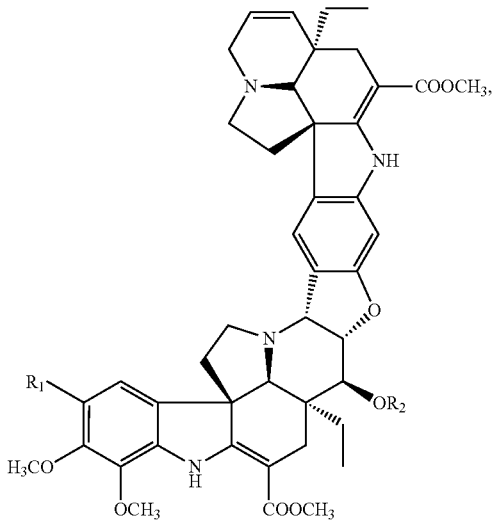

where, $R_1$ is OH, and $R_2$ is H; alternatively, $R_1$ is methoxy, and $R_2$ is hydrogen; alternatively, $R_1$ is methoxy, and $R_2$ is methyl;

formula I-7

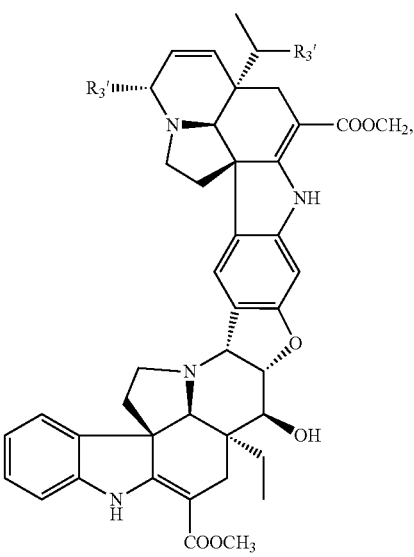

where, $R_1'$ is H, and $R_3'$ is H; alternatively, $R_1'$ is OH, and $R_3'$ is H; alternatively, $R_1'$ is H, and $R_3'$ is —OAc;

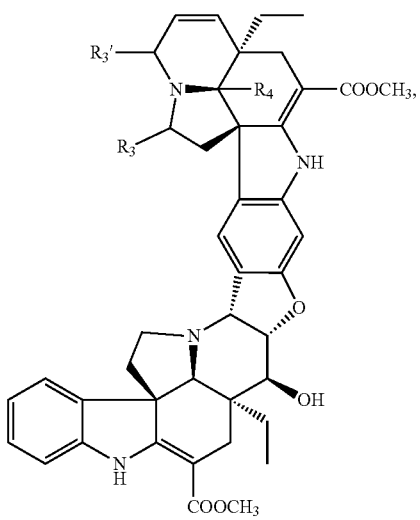

formula I-8 where, $R_3$ is hydrogen, $R_3'$ is =O, and $R_4$ is hydrogen; alternatively, $R_3$ is hydrogen, $R_3'$ is =O, and $R_4$ is hydroxyl; alternatively, $R_3$ is =O, $R_3'$ is hydrogen, and $R_4$ is hydrogen; and

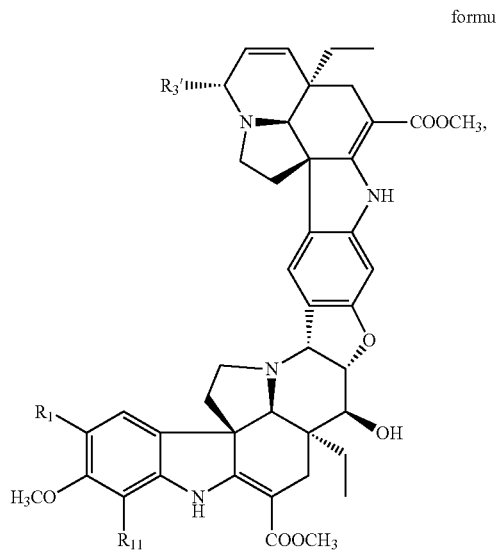

formula I-9 where, $R_1$ is hydrogen, $R_{11}$ is hydrogen, and $R_3'$ is hydrogen; alternatively, $R_1$ is hydrogen, $R_{11}$ is hydroxyl, and $R_3'$ is hydrogen; alternatively, $R_1$ is hydrogen, $R_{11}$ is methoxy, and $R_3'$ is hydrogen; alternatively, $R_1$ is hydroxyl, $R_{11}$ is hydrogen, and $R_3'$ is hydrogen; alternatively, $R_1$ is methoxy, $R_{11}$ is hydrogen, and $R_3'$ is hydrogen; alternatively, $R_1$ is hydroxyl, $R_{11}$ is methoxy, $R_3'$ is =O.

Preferably, the inorganic salt may be selected from the group consisting of a hydrochloride, a hydrobromide, a nitrate, a sulfate and a phosphate.

Preferably, the organic salt may be selected from the group consisting of a tartrate, a citrate, a formate, an acetate and an oxalate.

The present disclosure further provides a preparation method of the furan-aspidospermine dimer, including the following steps:

conducting leaching, extraction and gradient elution successively on a plant selected from the group consisting of the genus *Ervatamia* and the genus *Melodinus* to obtain the furan-aspidospermine dimer.

The present disclosure further provides use of the furan-aspidospermine dimer or the pharmaceutically acceptable salt thereof in preparation of a drug for treating an immune disease.

The present disclosure further provides a pharmaceutical composition, including the furan-aspidospermine dimer or the pharmaceutically acceptable salt thereof and a pharmaceutically acceptable carrier.

Preferably, the furan-aspidospermine dimer or the pharmaceutically acceptable salt thereof may have a mass percentage content of greater than or equal to 10% in the pharmaceutical composition.

The present disclosure provides the furan-aspidospermine dimer or the pharmaceutically acceptable salt thereof, having the structure as shown in formula I; where $R_1$ and $R_1'$ each are independently selected from the group consisting of hydrogen, hydroxyl and $C_{1-6}$ alkoxy; n is a positive integer ranging from 0 to 4; $R_2$, $R_2'$ and $R_2''$ each are independently selected from the group consisting of hydrogen and $C_{1-6}$ alkyl; $R_3$ and $R_3'$ each are independently selected from the group consisting of hydrogen, hydroxyl and =O; $R_4$ is selected from the group consisting of hydrogen and hydroxyl; $R_1$ has no substituent or is =O; A-B is selected from the group consisting of —$CH_2$—$CH_2$—, —CH=CH—, —HOCH—CHOH—, —$CH_2$—CHOH— and

;

and the pharmaceutically acceptable salt thereof is selected from the group consisting of the organic salt and the inorganic salt substituted at positions $R_2$ and $R_2''$. In the present disclosure, the formula I is a dimer formed by ligation of two aspidospermine monomers through furan rings; compared with an aspidospermine dimer, tabernaemontines A-L, which has an opened furan ring without activity, this indicates that the furan ring is a key group for the activity. In addition, neither the furan-ringed aspidospermine, Corynantheine, nor the furan-ringed aspidospermine, Ibogabisindole, have the activity of inhibiting M2 polarization in macrophages. This further confirms that the aspidospermine monomer is also an essential unit for activity, that is, the rigid ligation between the aspidospermine monomer and the furan ring is a basic skeleton of the activity.

DETAILED DESCRIPTION OF THE EMBODIMENTS

Figure 1:
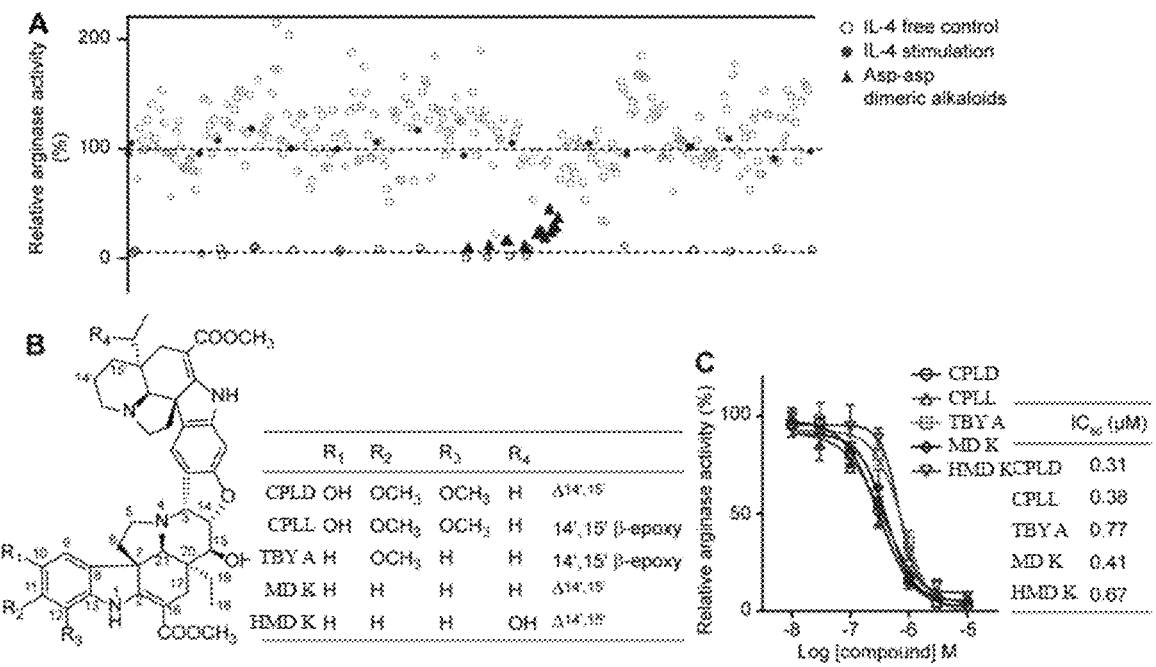
FIG. 1 shows a data graph of an activated immune assay for CPLD, CPLL, TBYA, MDK and HMD.

The present disclosure provides a furan-aspidospermine dimer or a pharmaceutically acceptable salt thereof, having a structure as shown in formula I:

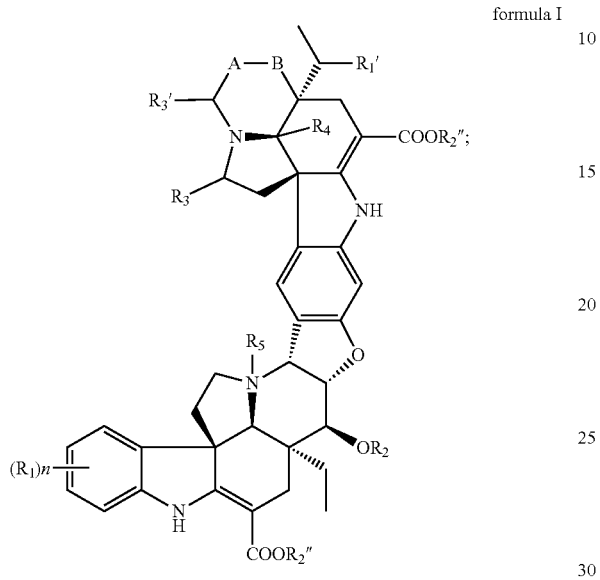

formula I where
- $R_1$ and $R_1{'}$ each are independently selected from the group consisting of hydrogen, hydroxyl and $C_{1-6}$ alkoxy; n is a positive integer ranging from 0 to 4;
- $R_2$, $R_2{'}$ and $R_2{''}$ each are independently selected from the group consisting of hydrogen and $C_{1-6}$ alkyl; $R_3$ and $R_3{'}$ each are independently selected from the group consisting of hydrogen, hydroxyl and =O;
- $R_4$ is selected from the group consisting of hydrogen and hydroxyl; $R_5$ is has no substituent or is =O;
- A-B is selected from the group consisting of —CH$_2$—CH$_2$—, —CH=CH—, —HOCH—CHOH—, —CH$_2$—CHOH— and

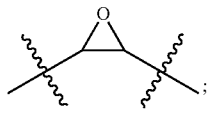 [SMILES: *C1OC1*]

;

and
the pharmaceutically acceptable salt thereof is selected from the group consisting of an organic salt and an inorganic salt substituted at positions $R_2{'}$ and $R_2{''}$.

In the present disclosure, when A-B is

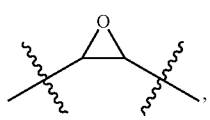 [SMILES: *C1OC1*]

, the furan-aspidospermine dimer or the pharmaceutically acceptable salt thereof has a structure preferably as shown in formula I-1 to formula I-4:

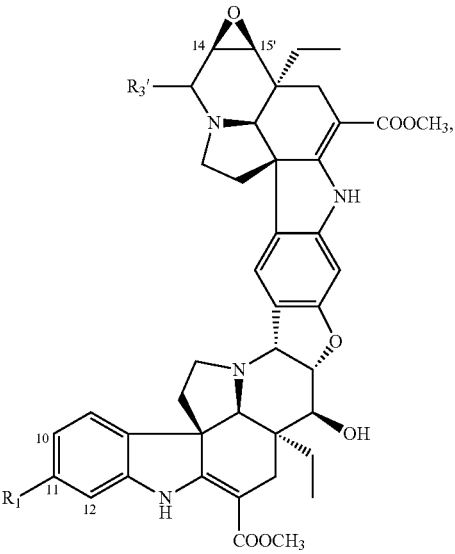

formula I-1 where, $R_1$ is hydrogen, and $R_3{'}$ is hydrogen (denoted as a compound 1); alternatively, $R_1$ is methoxy, and $R_3{'}$ is hydrogen (denoted as taberyunine A or TBY A); alternatively, $R_1$ is hydrogen, and $R_3{'}$ is =O (denoted as a compound 2);

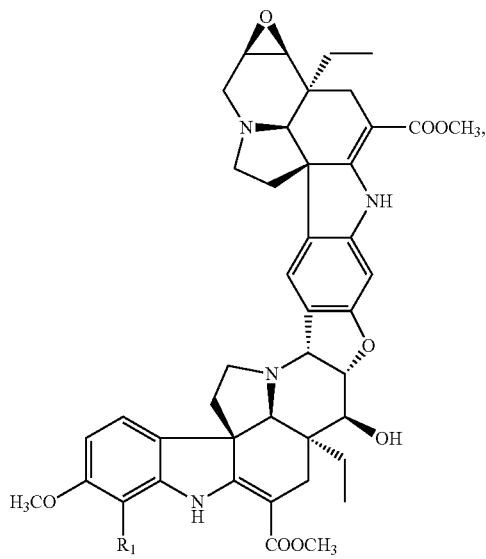

formula I-2 where, $R_1$ is selected from the group consisting of the hydroxyl (denoted as a taberyunine C) and methoxy (denoted as a 10-dehydroxyl-conophylline);

formula I-3

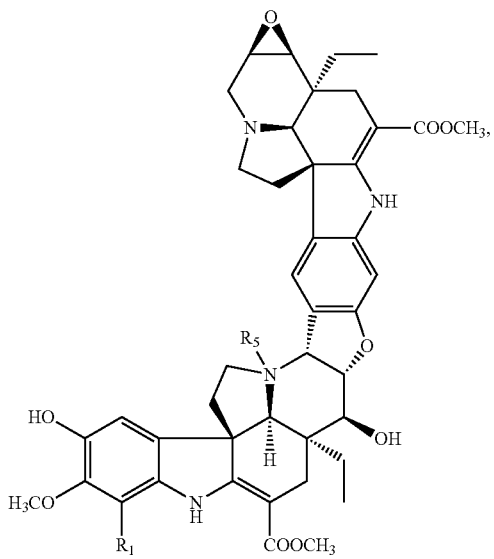

where, R₁ is hydrogen, and R₅ has no substituent (denoted as a compound 3); alternatively, R₁ is methoxy, and R₅ has no substituent (denoted as conophylline (CPLL)); alternatively, R₁ is methoxy, and R₅ is =O (denoted as a compound 4); and formula I-4

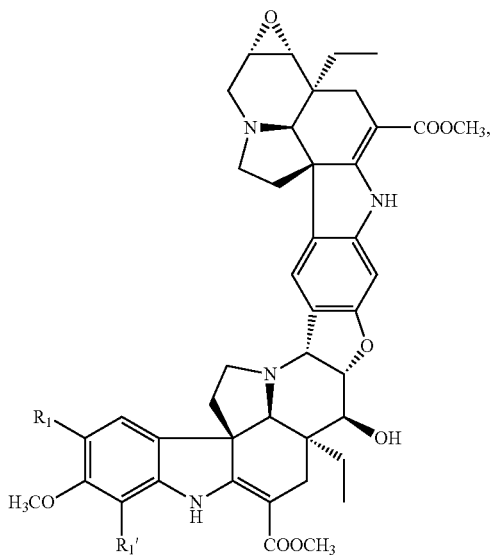

where, R₁ is OH and R₁' is H (denoted as a compound 5); or R₁ is H and R₁' is hydroxyl (denoted as a compound 6); or R₁ is OH and R₁' is methoxy (denoted as a compound 7).

In the present disclosure, when A-B is —CH₂—CHOH—, there may be hydroxyl β-OH located at position B in —CH₂—CHOH—; and the furan-aspidospermine dimer or the pharmaceutically acceptable salt thereof has a structure preferably as shown in formula I-5:

formula I-5 where, R₃' is =O (denoted as a compound 8);

when A-B is —HOCH—CHOH—, there are α-OH located at position A and the β-OH located at position B in —HOCH—CHOH—; and the furan-aspidospermine dimer or the pharmaceutically acceptable salt thereof has a structure preferably as shown in formula I-5:

formula I-5 where, R₃' is hydrogen (denoted as conophyllinine).

In the present disclosure, when A-B is —CH=CH—, the furan-aspidospermine dimer or the pharmaceutically acceptable salt thereof has a structure preferably as shown in formula I-6 to formula I-9:

formula I-6

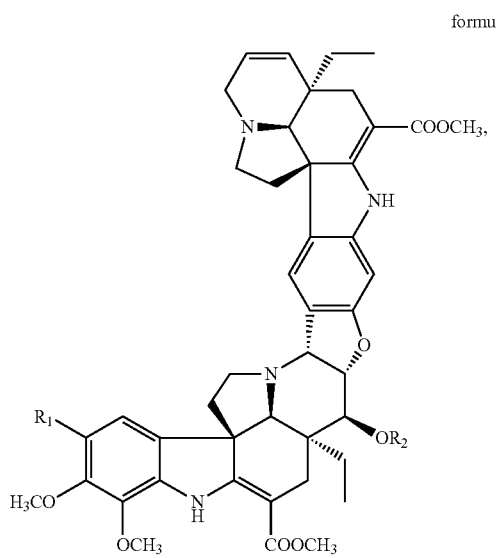

where, $R_1$ is OH, and $R_2$ is H (denoted as conophyllidine (CPLD)); alternatively, $R_1$ is methoxy, and $R_2$ is H (denoted as 10-O-methyl-conophyllidine); alternatively, $R_1$ is methoxy, and $R_2$ is methyl (10,15-dimethyl-conophyllidine);

formula I-7

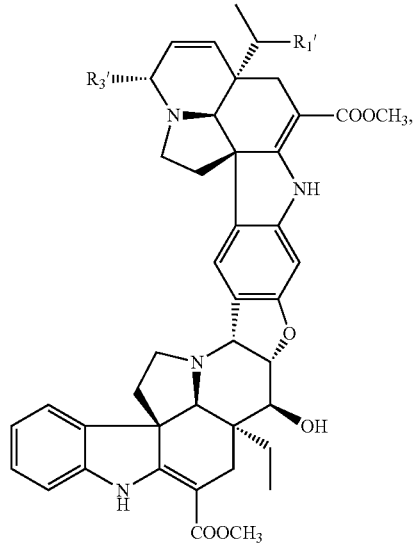

where, $R_1'$ is H, and $R_3'$ is H (denoted as melodinine K (MD K)); alternatively, $R_1'$ is OH, and $R_3'$ is H (denoted as 19'-hydroxymelodinineK (HMD K)); alternatively, $R_1'$ is H, and $R_3'$ is —OAc (denoted as 3'-acetonyl-melodinine K);

formula I-8

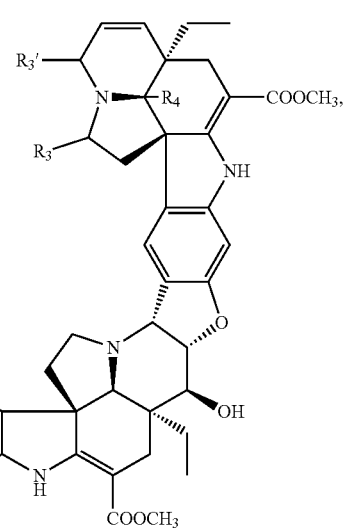

where, $R_3$ is hydrogen, $R_3'$ is =O, and $R_4$ is hydrogen (denoted as a compound 9); alternatively, $R_3$ is hydrogen, $R_3'$ is =O, and $R_4$ is hydroxyl (denoted as a compound 10); alternatively, $R_3$ is =O, $R_3'$ is hydrogen, and $R_4$ is hydrogen (denoted as a compound 11); and formula I-9

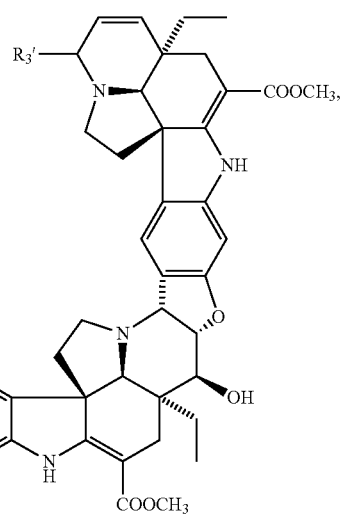

where, $R_1$ is H, $R_{11}$ is hydrogen, and $R_3'$ is hydrogen (denoted as taberyunine B); alternatively, $R_1$ is H, $R_{11}$ is hydroxyl, and $R_3'$ is hydrogen (denoted as a compound 12); alternatively, $R_1$ is H, $R_{11}$ is methoxy, and $R_3'$ is hydrogen (denoted as a compound 13); alternatively, $R_1$ is hydroxyl, $R_{11}$ is hydrogen, and $R_3'$ is hydrogen (denoted as a compound 14); alternatively, $R_1$ is methoxy, $R_{11}$ is hydrogen, and $R_3'$ is hydrogen (denoted as a compound 15); alternatively, $R_1$ is hydroxyl, $R_{11}$ is methoxy, $R_3'$ is =O (denoted as a compound 16).

In the present disclosure, the inorganic salt is selected from the group consisting of a hydrochloride, a hydrobromide, a nitrate, a sulfate and a phosphate.

In the present disclosure, the organic salt is selected from the group consisting of a tartrate, a citrate, a formate, an acetate and an oxalate.

The present disclosure further provides a preparation method of the furan-aspidospermine dimer, including the following steps:

conducting leaching, extraction and gradient elution successively on a plant selected from the group consisting of the genus *Ervatamia* and the genus *Melodinus* to obtain the furan-aspidospermine dimer.

In the present disclosure, the plant of the genus *Ervatamia* is preferably *Ervatamia officinalis* Tsiang, *Ervatamia divaricata*, *Tabernaemontana corymbosa*, *Tabernaemontana bufalina*, and *Tabernaemontana pandacaqui*; the plant of the genus *Melodinus* is preferably *Melodinus suaveolens* or *Melodinus tenuicaudatus*.

In the present disclosure, the leaching is preferably conducted in an organic solvent; the organic solvent is preferably selected from the group consisting of an alcohol solvent, a ketone solvent, an ester solvent, an ether solvent and a halogenated alkane solvent, more preferably a $C_{1-6}$ alcohol, a $C_{3-6}$ ketone, a $C_{3-6}$ ester, a $C_{2-6}$ ether or a $C_{1-6}$ haloalkane; $C_{1-6}$ alcohol is preferably selected from the group consisting of methanol, ethanol, n-propanol, isopropanol, n-butanol, isobutanol, tert-butanol, n-amyl alcohol, isoamyl alcohol, cyclopentanol, n-hexanol and cyclohexanol; the $C_{3-6}$ ketone is preferably selected from the group consisting of acetone, methyl ethyl ketone and methyl isobutyl ketone; the $C_{3-6}$ ester is preferably selected from the group consisting of ethyl formate and ethyl acetate propionate; the $C_{2-6}$ ether is preferably selected from the group consisting of methyl ether and ether; and $C_{1-6}$ haloalkane is preferably selected from the group consisting of dichloromethane, chloroform and dichloroethane.

After the leaching, an obtained leaching solution is preferably concentrated under reduced pressure to obtain a total extract.

In the present disclosure, an extraction agent for the extraction is preferably ethyl acetate; and a process is preferably as follows: adjusting a pH value of the obtained total extract to 1.0-4.5, conducting extraction by the ethyl acetate; and adjusting the pH value of an obtained acid water layer to 7.0-11.0, and conducting secondary extraction by the ethyl acetate.

In the present disclosure, the gradient elution is preferably conducted by silica gel column chromatography; an elution machine used is preferably a chloroform-methanol system (1:0 to 0:1, v/v).

In the present disclosure, an extraction process of the compounds of the structures represented by formula I-1 to formula I-9 is as follows:

75 kg of dried leaves of *Tabernaemontana bovina* are pulverized and extracted with methanol for 3 times (3×20 L), an obtained extract is concentrated under reduced pressure and adjusted to a pH value of 2-3, followed by extraction with ethyl acetate twice; a pH value of an acid water layer obtained by extraction is adjusted to 7-9 and then extracted three times with an equal volume of the ethyl acetate, and an obtained ethyl acetate layer is combined and concentrated to obtain a total alkaloid (875 g). The obtained total alkaloid is subjected to silica gel column chromatography, and eluted with chloroform-methanol (1:0 to 1:1, v/v), and obtained fractions are combined to obtain fractions I to X. 246 g of the fraction III is eluted through an RP-18 medium-pressure column gradient (30% to 100% methanol) and divided into 12 fractions (III-1 to III-12). The III-10 (45 g) is eluted with 50% to 90% methanol by an RP-1 medium-pressure chromatographic column to obtain 7 small fractions (III-10-1 to III-10-7); where the III-10-7 is purified by gel (methanol) twice and further purified by high performance liquid chromatography (HPLC) preparation (60% to 75% acetonitrile) to obtain the compound 6. The III-11 (37 g) is further gradient-eluted by a 50% to 100% methanol solution by the RP-18 medium-pressure column to obtain 8 small fractions (III-11-1 to III-10-8); where the III-11-5 is purified by the gel (methanol) and further purified by the HPLC preparation (70% to 85% acetonitrile) to obtain the compound 15; the III-11-8 is purified by the gel (methanol) and further purified by the HPLC preparation (C18 preparative column, 60% to 75% acetonitrile) to obtain the compound 5. The III-12 (20 g) is continued for gradient elution (60% to 100% methanol) by the RP-18 medium-pressure chromatographic column to obtain 5 small fractions (III-12-1 to III-12-5); the III-12-4 is purified twice by the gel (methanol) and further purified by the HPLC preparation (C18 preparative column, 65% to 80% acetonitrile) to obtain the compound 16. The III-12-5 is subdivided by the gel (methanol) and further purified by the HPLC preparation (C18 preparative column, 65% to 80% acetonitrile) to obtain the 10-dihydroxyl-conophylline. The IV component (79 g) is gradient-eluted with a methanol-water solution (15% to 85%) through the RP-18 medium-pressure chromatographic column, and then divided into 7 fractions (IV-1 to IV-7). The IV-5 (16 g) is further gradient-eluted by the methanol-water solution (30% to 80%) through the RP-18 medium-pressure chromatographic column to obtain 5 small fractions (IV-5-1 to IV-5-5); where the IV-5-3 is purified by the gel (methanol) and further purified by the HPLC preparation (C18 preparative column, 45% to 60% acetonitrile) to obtain the conophyllinine; the IV-5-4 is purified by the gel (methanol) and further purified by the HPLC preparation (C18 preparative column, 45% to 60% acetonitrile) to obtain the compound 8.

Dried leaves (7.5 kg) of *T. divaricata* are crushed, extracted with methanol at room temperature for 3 times, and concentrated under reduced pressure to obtain a total extract. The total extract is adjusted to pH 2-3 and extracted with equal volume of ethyl acetate for 3 times; an obtained acid water layer is adjusted to a pH value of 7-9, and extracted three times with an equal volume of the ethyl acetate to obtain a total alkaloid (68 g); the total alkaloid is subjected to normal-phase silica gel column chromatography, eluted with a chloroform-methanol system (1:0 to 0:1, v/v), and combined to obtain 5 fractions (Fr. I to Fr. V). The Fr. II (25 g) is fractioned by the medium-pressure column chromatography and gradient-eluted with a methanol-water system (10% to 100%) to obtain 5 fractions (Fr. II-1 to Fr. II-5). The Fr. II-2 (2 g) is further segmented by the medium-pressure column chromatography and gradient-eluted with the methanol-water system (30% to 55%) to obtain 5 fractions (Fr. II-2-1 to Fr. II-2-5); the Fr. II-2-4 (0.5 g) is treated on a Sephadex LH-20 gel column and purified by the HPLC (50% to 65% acetonitrile) to obtain the compound 3. The Fr. II-3 (8.5 g) precipitates white columnar crystals; an obtained mother liquor (5 g) is separated by medium pressure, and then gradient-eluted by 10% to 80% methanol into 4 fractions (Fr. II-3-1 to Fr. II-3-4). The Fr. II-3-4 is purified by the HPLC (C18 preparative column, 45% to 60% acetonitrile) to obtain the compound 4. The Fr. II-4 (3.5 g) is segmented by medium pressure and gradient-eluted with the methanol-water system (45% to 65%) to obtain 7 fractions (Fr. II-4-1 to Fr. II-4-7). The Fr. II-4-5 (2.0 g) is treated with the Sephadex LH-20 gel column to obtain 4 fractions; where the Fr. II-4-5-3 is purified by HPLC (65% to 80% acetonitrile) to obtain the compound 7; the Fr. II-4-5-4 is purified by HPLC (C18 preparative column, 65% to 80% acetonitrile) to obtain the compound 12; the Fr. II-5 (0.7 g) is segmented by medium pressure, and then gradient-eluted by 45% to 65% methanol to obtain 8 fractions (Fr. II-5-1 to Fr. II-5-8); and the Fr. II-5-8 (0.1 g) is treated with the Sephadex LH-20 gel column and purified by HPLC (65% to 75% acetonitrile) to obtain the compound 13.

Dried stems and leaves of Tabernaemontana corymbosa (15 kg) are pulverized and extracted with methanol, and a total extract is obtained by concentration under reduced pressure. The total extract is completely dissolved with a 0.5% HCl solution, adjusted pH to 2-3, and extracted 3 times with equal volume of ethyl acetate; an obtained acid water fraction is adjusted to pH 9-10 with 10% ammonia water, extracted three times with an equal volume of the ethyl acetate, and ethyl acetate layers are combined and concentrated to obtain a total alkaloid (61.5 g). The total alkaloid is subjected to silica gel column chromatography and chloroform-acetone gradient elution (1:0 to 2:1), and 8 fractions (Fr. I to Fr. VIII) are obtained by combining the same fractions. The IV (11.3 g) is subjected to C18 medium-pressure preparation (MeOH to $H_2O$: 40%, 50%, 60%, 70% and 80%) to obtain five fractions IV-1 to IV-5. IV-4 (1.2 g) is subjected to C18 medium-pressure preparation (MeOH—$H_2O$, 40% to 65%), and high-pressure preparation (C18 column), followed by MeOH—$H_2O$ (60% to 70%) gradient elution to obtain the Taberyunine C. The Fr. VIII (20.3 g) is segmented by medium pressure (methanol water: 15% to 65%) to obtain two fractions VIII-I and VIII-II. The VIII-I (8.2 g) is subjected to silica gel column chromatography (chloroform-acetone, 5:1 to 0:1) to obtain 5 fractions. The VIII-I-2 (1.5 g) is subjected to silica gel column chromatography (chloroform-methanol, 20:1 to 9:1) to obtain VIII-I-2-1, followed by being further purified by HPLC (methanol-water: 40% to 55%) to obtain the conophyllidine and the conophylline. The VIII-I-5 (0.42 g) is purified by HPLC (methanol-water: 60% to 75%) to obtain the 10-dehydroxyl-conophylline. The VIII-II (4.7 g) is subjected to silica gel column chromatography (chloroform-methanol, 5:1 to 0:1) to obtain three fractions VIII-II-1 to VIII-II-3. VIII-II-1 (0.9 g) is subjected to silica gel column chromatography (chloroform-methanol, 10:1) to obtain VIII-II-1-1, and then purified by HPLC (methanol water: 70% to 85%) to obtain the taberyunine A and the taberyunine B.

Dried stems of M. suaveolens (28 kg) are crushed and extracted with methanol for 4 times (4×75 L), and an extract was recovered under reduced pressure to obtain a total extract. The total extract is adjusted to pH 2-3 and extracted with equal volume of ethyl acetate for 3 times; an obtained acid water layer is adjusted to a pH value of 7-9, and extracted three times with an equal volume of the ethyl acetate to obtain a total alkaloid (250 g); the total alkaloid is subjected to silica gel column chromatography, and then gradient-eluted with chloroform-acetone, to obtain 3 fractions (Fr. I to Fr. III). The Fr. II (3.0 g) is separated by medium pressure (30% to 80% methanol) to obtain nine fractions II-1 to II-9. The II-2 is separated by medium pressure (60% to 80% methanol) to obtain the compound melodinine K. The II-9 (1.1 g) is divided into 5 fractions by medium pressure, II-9-1 to II-9-5; the II-9-1 is divided into two fractions by Sephadex LH-20 dextran gel (100% methanol), namely II-9-1-1 to II-9-1-2. The II-9-1-1 is purified by HPLC (50% to 65% acetonitrile) to obtain the compound 10; the II-9-1-2 is purified by Sephadex LH-20 Sephadex (methanol) and HPLC (50% to 65% acetonitrile) to obtain the compound 2; II-9-2 is eluted by the Sephadex LH-20 Sephadex (methanol) and then purified by HPLC (45% to 60% acetonitrile) to obtain the compound 9; and the II-9-3 is purified by HPLC (55% to 70% acetonitrile) to obtain the compound 11.

Dried stems and leaves of M. suaveolens (3.0 kg) are crushed and soaked in 95% ethanol for 3 times for 24 h each time; obtained extracts are combined, the solvent is distilled off under reduced pressure, and an obtained crude extract is suspended in water. The crude extract is adjusted to pH 2-3 by adding 1% aqueous hydrochloric acid, stirred, and extracted with EtOAc; a pH value of an obtained aqueous layer is adjusted to pH 9-10 with a 10% aqueous ammonia solution, and then extracted with the EtOAc to obtain 9.8 g of a total alkaloid extract. The total alkaloid extract is mixed with 10 g of a silica gel, subjected to 100 g of silica gel chromatography, and gradient-eluted with petroleum ether-acetone (40:1 to 2:1) to obtain IV fractions. The fraction III (3.2 g) is eluted with an RP-18 reverse-phase column (acetonitrile-water, 5% to 40%) to obtain III-1 to III-3; where the III-3 is purified by HPLC to obtain the melodinine K; the fraction IV (0.8 g) is purified by HPLC (70% to 80% methanol) to obtain the compounds 3'-acetonyl-melodinine K and 19'-hydroxy-melodinine K.

Dried stems and leaves (14 kg) of Melodinus tenuicaudatus are treated with the same method as above, to obtain 17 g of a total alkaloid extract. The total alkaloid extract is subjected to silica gel column chromatography and chloroform-methanol gradient elution, and obtained approximate fractions are combined to obtain 5 fractions. The 4th fraction (2 g)) is subjected to silica gel column chromatography, elution with chloroform-methanol (15:1 to 8:1), and then silica gel atmospheric-pressure and medium-pressure column chromatography; an obtained product is repeatedly purified by elution systems such as petroleum ether/acetone (4:1), petroleum ether/ethyl acetate (3:1), chloroform/acetone (9:1) and methanol/water (60% to 80%), to obtain the compound melodinine K.

The obtained melodinine K, chloroform, perchloric acid and m-chloroperoxybenzoic acid are mixed, followed by conducting oxidation reaction under 0° C. to obtain the compound 1; a reaction formula is as follows:

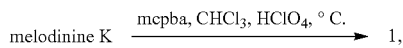

The obtained melodinine K is mixed with the m-chloroperoxybenzoic acid and the chloroform, and then mixed with trifluoroacetic anhydride and acetone, followed by conducting oxidation reaction and nucleophilic reaction under 0° C. to obtain the 3'-acetonyl-melodinine K; a reaction formula is as follows:

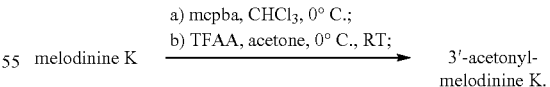

The conophyllidine, methyl iodide and acetonitrile are mixed, followed by conducting substitution reaction at room temperature to obtain the 10-O-methyl-conophyllidine; a reaction formula is as follows:

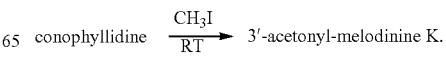

The conophyllidine, methyl iodide and acetonitrile are mixed, followed by conducting substitution reaction at 50° C. to obtain the 10,15-O-dimethyl-conophyllidine; a reaction formula is as follows:

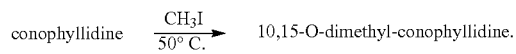

The present disclosure further provides use of the furan-aspidospermine dimer or the pharmaceutically acceptable salt thereof in preparation of a drug for treating an immune disease.

The present disclosure further provides a pharmaceutical composition, including the furan-aspidospermine dimer or the pharmaceutically acceptable salt thereof and a pharmaceutically acceptable carrier.

In the present disclosure, the furan-aspidospermine dimer or the pharmaceutically acceptable salt thereof has a mass percentage content of preferably ≥10%, more preferably ≥20%, and most preferably ≥50% in the pharmaceutical composition. There is no special limitation on a type of the pharmaceutically acceptable carrier, and types well-known to those skilled in the art can be used.

In the present disclosure, there is no special limitation on a dosage form of the pharmaceutical composition, and dosage forms well known to those skilled in the art can be used.

In the present disclosure, the pharmaceutical composition is preferably administered orally or parenterally. A daily dosage is preferably 1 mg to 1,000 mg. When a route of administration is oral administration, the pharmaceutical composition further includes preferably a pharmaceutical adjuvant; the pharmaceutical adjuvant includes preferably one or more of an excipient, a disintegrant, a binder, a lubricant, an antioxidant, a coating agent, a colorant, a fragrance and a surfactant; the pharmaceutical adjuvant in the pharmaceutical composition has a mass percentage content of preferably ≥10%, more preferably ≥20%, and most preferably ≥50%; and the pharmaceutical composition has a dosage form selected from the group consisting of preferably a granule, a capsule or a tablet. When the route of administration is parenteral administration, the pharmaceutical composition has an administration form selected from the group consisting of preferably an injection, an infusion and a suppository.

The furan-aspidospermine dimer or the pharmaceutically acceptable salt thereof, and a preparation method, use and a pharmaceutical composition provided by the present disclosure will be described in detail below in conjunction with examples, but should not be construed as limiting the protection scope of the present disclosure.

Example 1

75 kg of dried leaves of *Tabernaemontana bovina* were pulverized and extracted with methanol for 3 times (3×20 L), an obtained extract was concentrated under reduced pressure and adjusted to a pH value of 2-3, followed by extraction with ethyl acetate twice; a pH value of an acid water layer obtained by extraction was adjusted to 7-9 and then extracted three times with an equal volume of the ethyl acetate, and an obtained ethyl acetate layer was combined and concentrated to obtain a total alkaloid (875 g). The obtained total alkaloid was subjected to silica gel column chromatography, and eluted with chloroform-methanol (1:0 to 1:1, v/v), and obtained fractions were combined to obtain fractions I to X. 246 g of the fraction III was eluted through an RP-18 medium-pressure column gradient (30% to 100% methanol) and divided into 12 fractions (III-1 to II-12). The III-10 (45 g) was eluted by RP-1 medium-pressure column with 50% to 90% methanol to obtain 7 small fractions (III-10-1 to III-10-7); where the III-10-6 was separated by the gel (elution with methanol) and further purified by the HPLC preparation (C18 preparative column, 70% to 85% acetonitrile) to obtain the compound 14; the II-10-7 was purified by the gel (methanol) twice and further purified by the HPLC preparation (60% to 75% acetonitrile) to obtain the compound 6. The III-11 (37 g) was further gradient-eluted by a 50% to 100% methanol solution by the RP-18 medium-pressure column to obtain 8 small fractions (III-11-1 to III-10-8); where the III-11-5 was purified by the gel (methanol) and further purified by the HPLC preparation (70% to 85% acetonitrile) to obtain the compound 15; the III-11-8 was purified by the gel (methanol) and further purified by the HPLC preparation (C18 preparative column, 60% to 75% acetonitrile) to obtain the compound 5. The III-12 (20 g) was continued for gradient elution (60% to 100% methanol) by the RP-18 medium-pressure chromatographic column to obtain 5 small fractions (III-12-1 to III-12-5); the III-12-4 was purified twice by the gel (methanol) and further purified by the HPLC preparation (C18 preparative column, 65% to 80% acetonitrile) to obtain the compound 16. The III-12-5 was subdivided by the gel (methanol) and further purified by the HPLC preparation (C18 preparative column, 65% to 80% acetonitrile) to obtain the 10-dehydroxyl-conophylline. The IV component (79 g) was gradient-eluted with a methanol-water solution (15% to 85%) through the RP-18 medium-pressure chromatographic column, and then divided into 7 fractions (IV-1 to IV-7). The IV-5 (16 g) was further gradient-eluted by the methanol-water solution (30% to 80%) through the RP-18 medium-pressure chromatographic column to obtain 5 small fractions (IV-5-1 to IV-5-5); where the IV-5-3 was purified by the gel (methanol) and further purified by the HPLC preparation (C18 preparative column, 45% to 60% acetonitrile) to obtain the conophyllinine; the IV-5-4 was purified by the gel (methanol) and further purified by the HPLC preparation (C18 preparative column, 45% to 60% acetonitrile) to obtain the compound 8.

Dried leaves (7.5 kg) of *T. divaricata* were crushed, extracted with methanol at room temperature for 3 times, and concentrated under reduced pressure to obtain a total extract. The total extract was adjusted to pH 2-3 and extracted with equal volume of ethyl acetate for 3 times; an obtained acid water layer was adjusted to a pH value of 7-9, and extracted three times with an equal volume of the ethyl acetate to obtain a total alkaloid (68 g); the total alkaloid was subjected to normal-phase silica gel column chromatography, eluted with a chloroform-methanol system (1:0 to 0:1, v/v), and combined to obtain 5 fractions (Fr. I to Fr. V). The Fr. II (25 g) was fractioned by the medium-pressure column chromatography and gradient-eluted with a methanol-water system (10% to 100%) to obtain 5 fractions (Fr. II-1 to Fr. II-5). The Fr. II-2 (2 g) was further segmented by the medium-pressure column chromatography and gradient-eluted with the methanol-water system (30% to 55%) to obtain 5 fractions (Fr. II-2-1 to Fr. II-2-5); the Fr. II-2-4 (0.5 g) was treated on a Sephadex LH-20 gel column and purified by the HPLC (50% to 65% acetonitrile) to obtain the compound 3. The Fr. II-3 (8.5 g) precipitated white columnar crystals; an obtained mother liquor (5 g) was separated by medium pressure, and then gradient-eluted by 10% to 80% methanol into 4 fractions (Fr. II-3-1 to Fr. II-3-4). The Fr. II-3-4 was purified by the HPLC (C18 preparative column, 45% to 60% acetonitrile) to obtain the compound 4. The Fr. II-4 (3.5 g) was segmented by medium pressure and gradient-eluted with the methanol-water system (45% to 65%) to obtain 7 fractions (Fr. II-4-1 to Fr. II-4-7). The Fr. II-4-5 (2.0 g) was treated with the Sephadex LH-20 gel column to obtain 4 fractions; where the Fr. II-4-5-3 was purified by HPLC (65% to 80% acetonitrile) to obtain the compound 7; the Fr. II-4-5-4 was purified by HPLC (C18 preparative column, 65% to 80% acetonitrile) to obtain the compound 12; the Fr. II-5 (0.7 g) was segmented by medium pressure, and then gradient-eluted by 45% to 65% methanol to obtain 8 fractions (Fr. II-5-1 to Fr. II-5-8); and the Fr. II-5-8 (0.1 g) was treated with the Sephadex LH-20 gel column and purified by HPLC (65% to 75% acetonitrile) to obtain the compound 13.

Dried stems and leaves of *Tabernaemontana corymbosa* (15 kg) were pulverized and extracted with methanol, and a total extract was obtained by concentration under reduced pressure. The total extract was completely dissolved with a 0.5% HCl solution, adjusted pH to 2-3, and extracted 3 times with equal volume of ethyl acetate; an obtained acid water fraction was adjusted to pH 9-10 with 10% ammonia water, extracted three times with an equal volume of the ethyl acetate, and ethyl acetate layers were combined and concentrated to obtain a total alkaloid (61.5 g). The total alkaloid was subjected to silica gel column chromatography and chloroform-acetone gradient elution (1:0 to 2:1), and 8 fractions (Fr. I to Fr. VIII) were obtained by combining the same fractions. The IV (11.3 g) was subjected to C18 medium-pressure preparation (MeOH to H$_2$O: 40%, 50%, 60%, 70% and 80%) to obtain five fractions IV-1 to IV-5. IV-4 (1.2 g) was subjected to C18 medium-pressure preparation (MeOH—H$_2$O, 40% to 65%), and high-pressure preparation (C18 column), followed by MeOH—H$_2$O (60% to 70%) gradient elution to obtain the Taberyunine C. The Fr. VIII (20.3 g) was segmented by medium pressure (methanol water: 15% to 65%) to obtain two fractions VIII-I and VIII-II. The VIII-I (8.2 g) was subjected to silica gel column chromatography (chloroform-acetone, 5:1 to 0:1) to obtain 5 fractions. The VIII-1-2 (1.5 g) was subjected to silica gel column chromatography (chloroform-methanol, 20:1 to 9:1) to obtain VIII-I-2-1, followed by being further purified by HPLC (methanol-water: 40% to 55%) to obtain the conophyllidine and the conophylline. The VIII-I-5 (0.42 g) was purified by HPLC (methanol-water: 60% to 75%) to obtain the 10-dehydroxyl-conophylline. The VIII-II (4.7 g) was subjected to silica gel column chromatography (chloroform-methanol, 5:1 to 0:1) to obtain three fractions VIII-II-1 to VIII-II-3. VIII-II-1 (0.9 g) was subjected to silica gel column chromatography (chloroform-methanol, 10:1) to obtain VIII-II-1-1, and then purified by HPLC (methanol water: 70% to 85%) to obtain the taberyunine A and the taberyunine B.

Dried stems of *M. suaveolens* (28 kg) were crushed and extracted with methanol for 4 times (4×75 L), and an extract was recovered under reduced pressure to obtain a total extract. The total extract was adjusted to pH 2-3 and extracted with equal volume of ethyl acetate for 3 times, an obtained acid water layer was adjusted to a pH value of 7-9, and extracted three times with an equal volume of the ethyl acetate to obtain a total alkaloid (250 g); the total alkaloid was subjected to silica gel column chromatography, and then gradient-eluted with chloroform-acetone, to obtain 3 fractions (Fr. I to Fr. III). The Fr. 1 (3.0 g) was separated by medium pressure (30% to 80% methanol) to obtain nine fractions II-1 to II-9. The II-2 was separated by medium pressure (60% to 80% methanol) to obtain the compound melodinine K. The II-9 (1.1 g) was divided into 5 fractions by medium pressure, II-9-1 to II-9-5; the II-9-1 was divided into two fractions by Sephadex LH-20 dextran gel (100% methanol), namely II-9-1-1 to II-9-1-2. The II-9-1-1 was purified by HPLC (50% to 65% acetonitrile) to obtain the compound 10; the II-9-1-2 was purified by Sephadex LH-20 Sephadex (methanol) and HPLC (50% to 65% acetonitrile) to obtain the compound 2; II-9-2 was eluted by the Sephadex LH-20 Sephadex (methanol) and then purified by HPLC (45% to 60% acetonitrile) to obtain the compound 9; and the II-9-3 was purified by HPLC (55% to 70% acetonitrile) to obtain the compound 11.

Dried stems and leaves of *M. suaveolens* (3.0 kg) were crushed and soaked in 95% ethanol for 3 times for 24 h each time; obtained extracts were combined, the solvent was distilled off under reduced pressure, and an obtained crude extract was suspended in water. The crude extract was adjusted to pH 2-3 by adding 1% aqueous hydrochloric acid, stirred, and extracted with EtOAc; a pH value of an obtained aqueous layer was adjusted to pH 9-10 with a 10% aqueous ammonia solution, and then extracted with the EtOAc to obtain 9.8 g of a total alkaloid extract. The total alkaloid extract was mixed with 10 g of a silica gel, subjected to 100 g of silica gel chromatography, and gradient-eluted with petroleum ether-acetone (40:1 to 2:1) to obtain IV fractions. The fraction III (3.2 g) was eluted with an RP-18 reverse-phase column (acetonitrile-water, 5% to 40%) to obtain III-1 to III-3; where the III-3 was purified by HPLC to obtain the melodinine K; the fraction IV (0.8 g) was purified by HPLC (70% to 80% methanol) to obtain the compounds 3'-acetonyl-melodinine K and 19'-hydroxy-melodinine K.

Dried stems and leaves (14 kg) of *Melodinus tenuicaudatus* were treated with the same method as above, to obtain 17 g of a total alkaloid extract. The total alkaloid extract was subjected to silica gel column chromatography and chloroform-methanol gradient elution, and obtained approximate fractions were combined to obtain 5 fractions. The 4th fraction (2 g)) was subjected to silica gel column chromatography, elution with chloroform-methanol (15:1 to 8:1), and then silica gel atmospheric-pressure and medium-pressure column chromatography; an obtained product was repeatedly purified by elution systems such as petroleum ether/acetone (4:1), petroleum ether/ethyl acetate (3:1), chloroform/acetone (9:1) and methanol/water (60% to 80%), to obtain the compound melodinine K.

The obtained melodinine K, chloroform, perchloric acid and m-chloroperoxybenzoic acid were mixed, followed by conducting oxidation reaction under 0° C. to obtain the compound 1: a reaction formula was as follows:

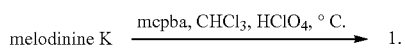

The obtained melodinine K was mixed with the m-chloroperoxybenzoic acid and the chloroform, and then mixed with trifluoroacetic anhydride and acetone, followed by conducting oxidation reaction and nucleophilic reaction under 0° C. to obtain the 3'-acetonyl-melodinine K; a reaction formula was as follows:

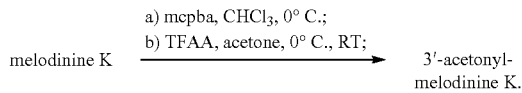

The conophyllidine, methyl iodide and acetonitrile were mixed, followed by conducting substitution reaction at room temperature to obtain the 10-O-methyl-conophyllidine; a reaction formula was as follows:

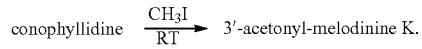

The conophyllidine, methyl iodide and acetonitrile were mixed, followed by conducting substitution reaction at 50° C. to obtain the 10,15-O-dimethyl-conophyllidine; a reaction formula was as follows:

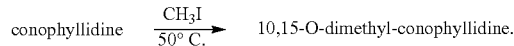

The spectral data of a series of furan-aspidospermine dimers obtained by the extraction of Example 1 are as follows:

The compound 1 is: a pale yellow powder, with a UV spectrum (MeOH) λ(max): 196, 245, and 330 nm; the nuclear magnetic $^1$H (800 MHz) and $^{13}$C (200 MHz) NMR (acetone-$d_6$) data are shown in Tables 1 and 2; and the mass spectrum ESI-MS m/z: 719 ([M+H]$^+$), the molecular formula is $C_{42}H_{46}N_4O_7$.

The compound 2 is: a pale yellow powder, with a UV spectrum (MeOH) λ(max): 191, 254, and 329 nm; the nuclear magnetic $^1$H (800 MHz) and $^{13}$C (200 MHz) NMR (acetone-$d_6$) data are shown in Tables 1 and 2; and the mass spectrum ESI-MS m/z: 733 ([M+H]$^+$), the molecular formula is $C_{42}H_{44}N_4O_8$.

The compound 3 is: a pale yellow powder, with a UV spectrum (MeOH) λ(max): 196, 254, and 328 nm; the nuclear magnetic $^1$H (600 MHz) and $^{13}$C (150 MHz) NMR (acetone-$d_6$) data are shown in Tables 1 and 2; and the mass spectrum ESI-MS m/z: 787 ([M+Na]$^+$), the molecular formula is $C_{43}H_{48}N_4O_9$.

The compound 4 is: a pale yellow powder, with a UV spectrum (MeOH) λ(max): 196, 254, 332 nm; the nuclear magnetic $^1$H (600 MHz) and $^{13}$C (150 MHz) NMR (acetone-$d_6$) data are shown in Tables 1 and 2; and the mass spectrum ESIMS m/z: 809.3405 [M−H], the molecular formula is $C_{44}H_{50}N_4O_{11}$.

The compound 5 is: a yellow powder, with a UV spectrum (MeOH) λ(max): 196, 248, and 330 nm; the nuclear magnetic $^1$H (600 MHz) and $^{13}$C (150 MHz) NMR (acetone-$d_6$) data are shown in Tables 1 and 2; and the mass spectrum ESIMS m/z: 765 [M+H]$^+$, the molecular formula is $C_{43}H_{48}N_4O_9$.

The compound 6 is: a pale yellow powder, with a UV spectrum (MeOH) λ(max): 196, 248, and 332 nm; the nuclear magnetic $^1$H (600 MHz) and $^{13}$C (150 MHz) NMR (acetone-$d_6$) data are shown in Tables 1 and 2; and the mass spectrum ESIMS m/z: 765 [M+H]$^+$, the molecular formula is $C_{43}H_{48}N_4O_9$.

The compound 7 is: a yellow powder, with a UV spectrum (MeOH) λ(max): 196, 254, and 332 nm; the nuclear magnetic $^1$H (600 MHz) and $^{13}$C (150 MHz) NMR (acetone-$d_6$) data are shown in Tables 1 and 2; and the mass spectrum ESIMS m/z: 795.3601 [M+H]$^+$, the molecular formula is $C_{44}H_{50}N_4O_{10}$.

The compound 8 is: a yellow powder, with a UV spectrum (MeOH) λ(max): 196, 240, 320, and 340 nm; the nuclear magnetic $^1$H (600 MHz) and $^{13}$C (150 MHz) NMR (CD$_3$OD) data are shown in Tables 1 and 2; and the mass spectrum ESIMS m/z: 810 [M+H]$^+$, the molecular formula is $C_{44}H_{50}N_4O_{11}$.

The compound 9 is: a pale yellow powder, with a UV spectrum (MeOH) λ(max): 198, 254, and 328 nm; the nuclear magnetic $^1$H (800 MHz) and $^{13}$C (200 MHz) NMR (acetone-$d_6$) data are shown in Tables 1 and 2; and the mass spectrum ESIMS m/z: 717 [M+H]$^+$, the molecular formula is $C_{42}H_{44}N_4O_7$.

The compound 10 is: a pale yellow powder, with a UV spectrum (MeOH) λ(max): 196, 254, and 332 nm; the nuclear magnetic $^1$H (600 MHz) and $^{13}$C (150 MHz) NMR (acetone-$d_6$) data are shown in Tables 1 and 2; and the mass spectrum ESIMS m/z: 733 [M+H]$^+$, the molecular formula is $C_{42}H_{44}N_4O_8$.

The compound 11 is: a pale yellow powder, with a UV spectrum (MeOH) λ(max): 195, 254, and 329 nm; the nuclear magnetic $^1$H (800 MHz) and $^{13}$C (200 MHz) NMR (acetone-$d_6$) data are shown in Tables 3 and 4; and the mass spectrum ESIMS m/z: 717 [M+H]$^+$, the molecular formula is $C_{42}H_{44}N_4O_7$.

The compound 12 is: a pale yellow powder, with a UV spectrum (MeOH) λ(max): 196, 243, and 331 nm; the nuclear magnetic $^1$H (500 MHz) and $^{13}$C (125 MHz) NMR (acetone-$d_6$) data are shown in Tables 3 and 4; and the mass spectrum ESIMS m/z: 749 [M+H]$^+$, the molecular formula is $C_{43}H_{48}N_4O_8$.

The compound 13 is: a pale yellow powder, with a UV spectrum (MeOH) λ(max): 196, 242, and 328 nm; the nuclear magnetic $^1$H (600 MHz) and $^{13}$C (150 MHz) NMR (acetone-$d_6$) data are shown in Tables 3 and 4; and the mass spectrum ESIMS m/z: 785.3526 [M+Na]$^+$, the molecular formula is $C_{44}H_{50}N_4O_8$.

The compound 14 is: a yellow powder, with a UV spectrum (MeOH) λ(max): 198, 250, and 326 nm; the nuclear magnetic $^1$H (600 MHz) and $^{13}$C (150 MHz) NMR (acetone-$d_6$) data are shown in Tables 3 and 4; and the mass spectrum ESIMS m/z: 749 [M+H]$^+$, the molecular formula is $C_{43}H_{48}N_4O_8$.

The compound 15 is: a yellow powder, with a UV spectrum (MeOH) λ(max): 198, 250, and 330 nm; the nuclear magnetic $^1$H (600 MHz) and $^{13}$C (150 MHz) NMR (acetone-$d_6$) data are shown in Tables 3 and 4; and the mass spectrum ESIMS m/z: 763 [M+H]$^+$, the molecular formula is $C_{44}H_{50}N_4O_8$.

The compound 16 is: a yellow powder, with a UV spectrum (MeOH) λ(max): 198, 245, and 335 nm; the nuclear magnetic $^1$H (600 MHz) and $^{13}$C (150 MHz) NMR (acetone-$d_6$) data are shown in Tables 3 and 4; and the mass spectrum ESIMS m/z: 793 [M+H]$^+$, the molecular formula is $C_{44}H_{48}N_4O_{10}$.

The taberyunine A is: a pale yellow powder, with a UV spectrum (MeOH) λ(max): 242, 330 nm; the nuclear magnetic $^1$H NMR (600 MHz, acetone-$d_6$) δ is: 7.40 (1H, s, H-9'), 6.58 (1H, s, H-12), 6.56 (1H, s, H-12'), 5.99 (1H, d, J=8.1 Hz, H-9), 5.92 (1H, d, J=8.1 Hz, H-10), 4.97 (1H, dd, J=8.0, 4.8 Hz, H-14), 4.88 (1H, d, J=8.0 Hz, H-3), 4.08 (1H, brd, J=4.8 Hz, H-15), 3.71 (3H, s, CO$_2$Me'), 3.69 (3H, s, CO$_2$Me), 3.65 (3H, s, 11-OMe), 0.90 (3H, t, J=7.2 Hz, H-18'), 0.66 (3H, t, J=7.2 Hz, H-18); $^{13}$C (150 MHz) NMR (acetone-$d_6$) data is shown in Table 5; and the mass spectrum HR-ESI-MS m/z: 749.3552 [M+H]$^+$, the molecular formula is $C_{43}H_{48}N_4O_8$.

The taberyunine C is: a white powder, with a UV spectrum (MeOH) λ(max): 241, 328 nm; the nuclear magnetic $^1$H NMR (600 MHz, acetone-$d_6$) δ is: 8.88 (1H, s, NH), 9.39 (1H, s, NH'), 7.42 (1H, s, H-9'), 6.57 (1H, s, H-12'), 5.99

(1H, d, J=8.4 Hz, H-10), 5.64 (1H, d, J=8.4 Hz, H-9), 4.97 (1H, dd, J=7.8, 4.8 Hz, H-14), 4.89 (1H, d, J=7.8 Hz, H-3), 4.08 (1H, brd, J=4.8 Hz, H-15), 3.72 (6H, s, C'O$_2$Me and CO$_2$Me), 3.73 (3H, s, 11-OMe), 0.92 (3H, t, J=7.8 Hz, H-18'), 0.68 (3H, t, J=7.2 Hz, H-18); $^{13}$C (150 MHz) NMR (acetone-d$_6$) data is shown in Table 5; the mass spectrum HRESIMS m/z: 765.3480 [M$^+$ H]$^+$, the molecular formula is C$_{43}$H$_{49}$N$_4$O$_9$.

The 10-Dehydroxyl-conophylline is: a white powder, with a UV spectrum (MeOH) λ(max): 248, 329 nm; the nuclear magnetic $^1$H (600 MHz) NMR (acetone-d$_6$) δ is: 8.88 (1H, s, NH), 9.39 (1H, s, NH'), 7.42 (1H, s, H-9'), 6.57 (1H, s, H-12'), 5.99 (1H, d, J=8.4 Hz, H-10), 5.64 (1H, d, J=8.4 Hz, H-9), 4.97 (1H, dd, J=7.8, 4.8 Hz, H-14), 4.89 (1H, d, J=7.8 Hz, H-3), 4.08 (1H, brd, J=4.8 Hz, H-15), 3.72 (6H, s, CO$_2$Me' and CO$_2$Me), 3.65 (3H, s, 11-OMe), 0.92 (3H, t, J=7.2 Hz, H-18'), 0.66 (3H, t, J=7.2 Hz, H-18); the mass spectrum ESI-MS m/z: 779.3623 [M$^+$ H]$^+$, the molecular formula is C$_{44}$H$_{50}$N$_4$O$_9$.

The Conophylline is: a white powder, with a UV spectrum (MeOH) λ(max): 243, 330 nm; the nuclear magnetic $^1$H NMR (acetone-d$_6$, 400 MHz) δ is: 8.78 (1H, s, NH), 4.84 (1H, d, J=7.7 Hz, H-3), 5.65 (11H, s, H-9), 4.93 (1H, dd, J=7.7, 4.3 Hz, H-14), 4.09 (1H, m, H-15), 0.70 (3H, t, J=7.1 Hz, H-18), 2.56 (1H, s, H-21), 3.70 (3H, s, 16-COOCH$_3$), 9.37 (1H, s, NH'), 7.19 (1H, s, H-9'), 6.58 (1H, s, H-12'), 3.16 (1H, m, H-14'), 0.76 (3H, t, J=7.2 Hz, H-18'), 2.66 (1H, s, H-21'), 3.71 (3H, s, 16'-COOCH$_3$), 3.72 (3H, s, 11'-OCH$_3$), 3.86 (3H, s, 12'-OCH$_3$); $^{13}$C (100 MHz) NMR (acetone-dc) data is shown in Table 5.

The Conophyllinine is: a yellow powder; the nuclear magnetic $^1$H NMR (500 MHz acetone-d$_6$,) 5 is: 8.77 (1H, s, NH), 5.75 (1H, s, H-9), 4.91 (1H, dd, J=7.6, 3.5 Hz, H-14), 4.83 (1H, d, J=7.6 Hz, H-3), 3.83 (3H, s, 12-OCH$_3$), 3.72 (3H, s, 11'-OCH$_3$), 3.68 (3H, s, 16-COOCH$_3$), 0.68 (3H, t, J=7.5 Hz, H-18), 9.26 (1H, s, NH'), 7.38 (1H, s, H-9'), 6.58 (1H, s, H-12'), 3.70 (3H, s, 16'-COOCH$_3$), 0.82 (3H, t, J=7.5 Hz, H-18'); $^{13}$C (125 MHz) NMR (acetone-d$_6$) data is shown in Table 5.

The Conophyllidine is: a pale yellow powder, with a UV spectrum (MeOH) λ(max): 242, 330 nm; the nuclear magnetic $^1$H NMR (acetone-d$_6$, 400 MHz) δ is: 9.37 (1H, s, NH'), 8.77 (1H, s, NH), 7.40 (1H, s, H-9'), 6.59 (1H, s, H-12'), 5.62 (1H, s, H-9), 4.93 (1H, dd, J=7.6, 3.6 Hz, H-14), 4.82 (1H, d, J=7.6 Hz, H-3), 4.05 (1H, d, J=3.6 Hz, H-15), 3.86 (3H, s, 12'-OCH$_3$), 3.72 (3H, s, 11'-OCH$_3$), 3.71 (3H, s, 16'-COOCH$_3$), 3.70 (3H, s, 16-COOCH$_3$), 0.70 (3H, t, J=7.4 Hz, H-18), 0.69 (3H, t, J=7.4 Hz, H-18'); $^{13}$C (acetone-d$_6$) NMR (100 MHz) data is shown in Table-5.

The 10-O-methyl-conophyllidine is: a pale yellow powder, with a UV spectrum (MeOH) λ(max): 242, 330 nm; the nuclear magnetic $^1$H (400 MHz) NMR (acetone-d$_6$) δ is: 9.29 (1H, s, NH), 6.20 (1H, d, J=7.2 Hz, H-9), 6.46 (1H, d, J=7.2 Hz, H-9), 7.01 (1H, d, J=7.2 Hz, H-11), 7.00 (1H, d, J=7.2, H-12), 5.01 (1H, dd, J=7.8, 3.6 Hz, H-14), 4.07 (1H, d, J=3-6 Hz, H-15), 4.83 (1H, d, H-3), 7.46 (1H, s, H-9'), 6.56 (1H, s, H-12'), 5.87 (2H, overlap, H-14'/15'), 3.77 (3H, s, COOCH$_3$), 3.66 (3H, s, C'OOC'H$_3$), 2.08 (3H, s, CH$_2$COCH$_3$), 0.84 (3H, t, J=7.4 Hz, H-18'), 0.67 (3H, t, J=7.4 Hz, H-18); the mass spectrum HRESIMS m/z: 849.4075 [M$^+$ H]$^+$, the molecular formula is C$_{48}$H$_{56}$N$_4$O$_{10}$.

The 10,15-O-dimethyl-conophyllidine is: a pale yellow powder, with a UV spectrum (MeOH) λ(max): 242, 330 nm; the mass spectrum HRESIMS m/z: 863.4231 [M$^+$ H]$^+$, the molecular formula is C$_{49}$H$_{58}$N$_4$O$_{10}$.

The Melodinine K is: a white powder; with a UV spectrum (MeOH) λ(max): 242, 330 nm; the nuclear magnetic $^1$H NMR (600 MHz, acetone-d$_6$) δ is: 9.27 (1H, s, NH), 9.39 (1H, s, NH'), 7.46 (1H, s, H-9'), 6.99 (1H, d, J=7.2 Hz, H-11), 6.94 (1H, d, J=7.2 Hz, H-12), 6.58 (1H, s, H-12'), 6.40 (1H, d, J=7.2 Hz, H-10), 6.11 (1H, d, J=7.2 Hz, H-9), 5.89 (2H, overlap, H-14'/15'), 5.00 (1H, dd, J=7.8, 3.6 Hz, H-14), 4.89 (1H, d, J=7.6 Hz, H-3), 4.07 (1H, dd, J=3.6 Hz, H-15), 3.72 (3H, s, C'O$_2$Me'), 3.71 (3H, s, CO$_2$Me), 0.82 (3H, t, J=7.2 Hz, H-18'), 0.67 (3H, t, J=7.2 Hz, H-18); $^{13}$C (150 MHz) NMR (acetone-&) data is shown in Table 6; the mass spectrum ESI-MS m/z: 703 [M$^+$ H]$^+$, the molecular formula is C$_{42}$H$_{46}$N$_4$O$_6$.

The 19'-Hydroxy-melodinine K is: a white powder; with a UV spectrum (MeOH) λ(max): 242, 330 nm; the nuclear magnetic $^1$H NMR (acetone-dc, 400 MHz) δ is: 9.24 (OH, s, NH), 9.33 (1H, s, NH), 7.43 (1H, s, H-9'), 6.96 (1H, t, J=7.3 Hz, H-11), 6.91 (1H, d, J=7.3 Hz, H-12), 6.56 (1H, s, H-12'), 6.54 (1H, t, J=7.3 Hz, H-10), 6.05 (1H, d, J=7.3 Hz, H-9), 5.85 (2H, overlap, H-14'/15'), 4.93 (1H, dd, J=7.8, 3.6 Hz, H-14), 4.83 (1H, d, J=7.8 Hz, H-3), 4.05 (1H, d, J=3.6 Hz, H-15), 3.77 (3H, s, COOCH$_3$), 3.69 (3H, s, C'OOC'H$_3$), 3.55 (1H, q, J=6.5 Hz), 1.00 (3H, d, J=6.6 Hz, H-18'), 0.65 (3H, t, J=7.8 Hz, H-18); $^{13}$C (150 MHz) NMR (acetone-d$_6$) data is shown in Table 6; the mass spectrum HR-ESI-MS m/z: 719.3443 [M$^+$ H]$^+$, the molecular formula is C$_{42}$H$_{46}$N$_4$O$_7$.

The 3'-acetonyl-melodinine K is: a white powder; with a UV spectrum (MeOH) λ(max): 330, 247 nm; the nuclear magnetic $^1$H (600 MHz) NMR (acetone-d$_6$) δ is: 9.49 (1H, s, NH), 9.29 (1H, s, NH), 7.46 (1H, s, H-9'), 7.01 (1H, t, J=7.2, H-11), 7.00 (1H, d, J=7.2, H-12), 6.56 (1H, s, H-12'), 6.46 (1H, t, J=7.2, H-10), 6.20 (1H, d, J=7.2 Hz, H-9), 5.87 (2H, overlap, H-14'/15'), 4.98 (1H, dd, J=7.8, 3.6 Hz, H-14), 4.83 (1H, s, H-3), 4.07 (1H, dd, J=3.6 Hz, H-15), 3.77 (3H, s, COOCH$_3$), 3.66 (3H, s, C'OOC'H$_3$), 2.08 (3H, s, CH$_2$COCH$_3$), 0.84 (3H, t, J=7.4 Hz, H-18'), 0.67 (3H, t, J=7.4 Hz, H-18); $^{13}$C (150 MHz) NMR (acetone-d$_6$) data is shown in Table 6; the mass spectrum HRESIMS m/z: 759.3761 [M$^+$ H]$^+$, the molecular formula is C$_{45}$H$_{50}$N$_4$O$_7$.

The taberyunine B is: a pale yellow powder, with a UV spectrum (MeOH) λ(max): 204, 242, 330 nm; the nuclear magnetic $^1$H NMR (600 MHz) 6 is: 9.23 (1H, s, NH), 9.39 (1H, s, NH'), 7.44 (1H, s, H-9'), 6.57 (2H, s, H-12/12'), 5.99 (1H, d, J=8.0 Hz, H-9), 5.91 (1H, d, J=8.0 Hz, H-10), 5.80 (2H, overlap, H-14'/15'), 4.95 (1H, dd, J=7.8, 4.8 Hz, H-14), 4.89 (1H, d, J=7.8 Hz, H-3), 4.06 (1H, d, J=4.8 Hz, H-15), 3.70 (3H, s, C'OOC'H$_3$), 3.69 (3H, s, COOCH$_3$), 3.63 (3H, s, 11-OMe), 0.84 (3H, t, J=7.2 Hz, H-18'), 0.66 (3H, t, J=7.2 Hz, H-18); $^{13}$C (150 MHz) NMR (acetone-d$_6$) data is shown in Table 6; the mass spectrum HRESIMS m/z: 733.3612 [M$^+$ H]$^+$, the molecular formula is C$_{43}$H$_{49}$N$_4$O$_7$.

Tables 1-6 show NMR data attribution of a series of furan-aspidospermine dimers obtained by the extraction of Example 1:

TABLE 1

Data attribution of $^1$H NMR of compounds 1-10 (acetone-$d_6$)

| No. | $\delta_H$ 1[b] | $\delta_H$ 2[b] | $\delta_H$ 3[a] | $\delta_H$ 4[a] | $\delta_H$ 5[a] | $\delta_H$ 6[a] | $\delta_H$ 7[a] | $\delta_H$ 8(CD$_3$OD)[a] | $\delta_H$ 9[b] | $\delta_H$ 10[a] |
|---|---|---|---|---|---|---|---|---|---|---|
| NH | 9.27 | 9.27 | 9.06, s | 8.78, s | 9.06, s | 8.88, s | 8.79, s |  | 9.27 | 9.24, s |
| 3 | 4.91, d, 7.8 | 4.94, d, 7.9 | 4.84, d, 7.8 | 5.34, d, 7.6 | 4.84, d, 7.4 | 4.90, d, 8.0 | 4.83, d, 7.6 | 4.82, overlap | 4.94, d, 7.8 | 4.95, d, 8.0 |
| 5 | 3.03, m 2.98, overlap | 3.03, overlap 2.92, overlap | 3.01, m 2.91, overlap | 3.60, m 3.46, m | 2.82, overlap 3.00, m | 2.94, m 3.00, dd, 8.4, 6.1 | 2.99, m 2.85, overlap | 2.70, td, 12.4, 4.2 3.01, t, 7.7 | 3.01, m 2.70, overlap | 2.99, m 3.14, m |
| 6 | 2.00, m 1.56, dd, 11.4, 4,3 | 1.56, dd, 11.2, 3.9 1.95, m | 1.96, overlap 1.55, dd, 11.3, 4.3 | 3.20, dd, 11.5, 5.6 1.80, dd, 11.5, 4.5 | 1.58, dd, 11.5, 4.2 1.92, m | 1.57, dd, 11.3, 4.2 1.96, m | 1.96, m 1.62, overlap | 1.56, dd, 11.5, 4.2 1.96, m | 1.99, m 1.55, dd, 11.3, 4.2 | 1.46, dd, 11.2, 4.2 1.95, m |
| 9 | 6.13, d, 7.5 | 6.14, d, 7.5 | 5.84, s | 5.36, s | 5.82, s | 5.66, d, 8.1 | 5.63, s | 5.57, s | 6.14, d, 7.5 | 6.41, d, 7.5 |
| 10 | 6.44, t, 7.4 | 6.45, t, 7.5 |  |  |  | 6.03, d, 8.1 |  |  | 6.43, t, 7.5 | 6.48, t, 7.5 |
| 11 | 7.03, t, 7.4 | 7.05, t, 7.5 |  |  |  |  |  |  | 7.03, t, 7.5 | 6.97, t 7.5 |
| 12 | 6.96, d, 7.5 | 6.96, d, 7.5 | 6.69, s |  | 6.69, s |  |  |  | 6.95, d, 7.5 | 6.89, d, 7.5 |
| 14 | 4.99, dd, 7.8, 3.5 | 5.02, dd, 7.9, 3.5 | 4.93, dd, 7.8, 3.4 | 5.32, dd, 7.6, 3.2 | 4.92, dd, 7.4, 3.2 | 4.99, dd, 8.0, 3.5 | 4.93, dd, 7.6, 3.4 | 4.91, m | 5.04, dd, 7.8, 3.5 | 5.01, dd, 8.0, 3.5 |
| 15 | 4.10, dd, 10.4, 3.5 | 4.10, dd, 10.7, 3.5 | 4.08, dd, 9.8, 3.4 | 4.14, d, 3.2 | 4.10, dd, 9.2, 3.2 | 4.08, dd, 10.5, 3.5 | 4.11, dd, 9.8, 3.4 | 4.12, d, 3.6 | 4.10, dd, 10.5, 3.5 | 4.06, dd, 10.6, 3.5 |
| 17 | 2.68, d, 15.6 2.56, overlap | 2.69, d, 15.2 2.56, d, 15.2 | 2.65, d, 15.1 2.54, d, 15.1 | 3.66, d, 15.5 2.64, d, 15.5 | 2.49, d, 15.4 2.68, d, 15.4 | 2.54 overlap 2.65, dd, 14.6, 2.0 | 2.66, d, 15.6 2.56, d, 15.6 | 2.47, d, 15.2 2.65, d, 15.2 | 2.70, d, 15.6 2.57, overlap | 2.66, d, 15.5 2.53, d, 15.5 |
| 18 | 0.68, t, 7.2 | 0.68, t, 7.3 | 0.67, t, 7.3 | 0.69, t, 7.3 | 0.68, t, 7.2 | 0.68, t, 7.3 | 0.68, t, 7.3 | 0.69, t, 7.1 | 0.69, t, 7.3 | 0.67, t, 7.3 |
| 19 | 1.09, m 0.76, m | 0.78, m 1.09, m | 1.06, m 0.79, m | 1.21, m 0.89, m | 0.81, overlap 1.06, m | 0.77, m 1.10, m | 1.09, m 0.78, overlap | 0.76, m 1.08, m | 1.11, m 0.77, m | 0.73, m 1.09, m |
| 21 | 2.54, s | 2.54, s | 2.57, s | 3.32, s | 2.57, br s | 2.49, br s | 2.58, overlap | 2.49, s | 2.56, s | 2.53, s |
| COOCH$_3$ | 3.71, s | 3.73, s | 3.68, s | 3.75, s | 3.70, s | 3.73, s | 3.73, s | 3.72, s | 3.72, s | 3.69, s |
| 11-OCH$_3$ |  |  | 3.72, s | 3.72, s | 3.75, s | 3.71, s | 3.71, s | 3.72, s |  |  |
| 12-OCH$_3$ |  |  |  | 3.89, s |  |  | 3.89, s | 3.86, s |  |  |
| NH' | 9.36, s | 9.56, s | 9.35, s | 9.57, s | 9.36, s | 9.40, s | 9.38, s |  | 9.57, s | 9.60, s |
| 3' |  | 3.47, d, 12.9 2.95, d, 12.9 | 3.44, d, 12.9 2.97, overlap | 3.45, d, overlap 2.91, d, 12.8 | 3.49, dd, 15.9, 2.1 2.99, overlap | 3.54, dd, 12.5, 5.5 2.87, overlap | 3.51, dd, 12.4, 5.5 2.86, overlap |  |  |  |
| 5' | 2.97, overlap 2.83, overlap | 4.37, overlap 3.37, overlap | 2.97, overlap 2.83, overlap | 2.96, overlap 2.81, overlap | 2.83, overlap 2.98, overlap | 2.61, td, 8.2, 4.2 2.92, m | 2.87, overlap 2.58, overlap | 4.08, dd, 12.4, 8.3 3.53, td, 12.4, 5.6 | 4.21, dd, 11.6, 7.4 3.42, overlap | 4.15, dd, 11.5, 7.4 3.71, m |
| 6' | 1.97, overlap 1.68, dd, 11.4, 4.6 | 1.83, overlap 1.80, overlap | 1.96, overlap 1.64, dd, 11.4, 4.6 | 1.98, m 1.69, dd, 11.5, 4.6 | 1.88, m 1.64, dd, 11.2, 4.4 | 1.92, m 1.69, dd, 11.3, 4.2 | 1.90, m 1.64, overlap | 2.10, m 1.77, dd, 12.4, 5.6 | 2.02, m 1.98, m | 2.10, m 1.94, m |
| 9' | 7.43, s | 7.75, s | 7.38, s | 7.75, s | 7.42, s | 7.40, s | 7.35, s | 7.32, s | 7.71, s | 7.88, s |
| 12' | 6.57, s | 6.63, s | 6.56, s | 6.71, s | 6.59, s | 6.57, s | 6.60, s | 6.53, s | 6.66, s | 6.60, s |
| 14' | 3.19, dd, 3.9, 1.2 | 3.50, d, 3.9 | 3.16, d, 3.8 | 3.17, d, 3.8 | 3.78, overlap | 3.50, dd, 5.6, 3.8 | 3.46, d, 3.8 | 2.50, overlap 2.75, overlap | 5.8, d, 9.9 | 5.87, overlap |
| 15' | 3.04, d, 3.9 | 3.70, overlap | 2.97, overlap | 2.98, d, 3.8 | 3.10, d, 3.9 | 3.15, d, 3.8 | 309, d, 3.8 | 4.16, m | 6.65, overlap | 6.64, overlap |
| 17' | 2.66, d, 14.4 2.59, d, 14.4 | 2.80, overlap 2.55, d 15.2 | 2.61, d, 14.4 2.56, d, 14.4 | 2.59, m, 2H | 2.58, d, 15.2 2.73, d, 15.2 | 2.54, overlap 2.67, d, 15.5, 1.7 | 2.60, d, 14.7 2.52, d, 14.7 | 2.22, d, 15.9 2.75, overlap | 2.10, d, 15.6 2.70, d, 15.6 | 2.66, d, 15.5 2.53, d, 15.5 |
| 18' | 0.90, t, 7.7 | 0.98, t, 7.3 | 0.77, t, 7.5 | 0.77, t, 7.2 | 0.78, t, 7.4 | 0.94, t, 7.4 | 0.79, t, 7.4 | 0.80, t, 7.2 | 0.92, t, 7.3 | 0.87, t, 7.3 |
| 19' | 1.17, m, 12.1, 2H | 1.10, m 0.78, m | 1.19, m, 2H | 1.22, m 1.12, m | 1.18, m 1.29, m | 1.19, m 1.37, m | 1.38, m 1.18, m | 1.14, m 1.21, m | 1.33, m 1.23, m | 1.65, m 1.31, m |
| 21' | 2.65, s | 3.72, overlap | 2.67, s | 2.67, s | 2.55, overlap | 2.56, br s | 2.56, overlap | 3.63, br s | 2.49, s | 4.18, s |
| COOCH$_3$ | 3.73, s | 3.75, s | 3.70, s | 3.75, s | 3.70 s | 3.73, s | 3.73, s | 3.79 s | 3.75, s | 3.70, s |

[a] recorded at 600 MHz;
[b] at 800 MHz

TABLE 2

Data attribution of ¹³C NMR of compounds 1-10 (acetone-d₆)

| No. | $\delta_C$ 1[b] | $\delta_C$ 2[b] | $\delta_C$ 3[a] | $\delta_C$ 4[b] | $\delta_C$ 5[a] | $\delta_C$ 6[a] | $\delta_C$ 7[a] | $\delta_C$ 8[a] (CD₃OD) | $\delta_C$ 9[b] | $\delta_C$ 10[a] |
|---|---|---|---|---|---|---|---|---|---|---|
| 2 | 164.8 s | 164.7 s | 166.4 s | 164.2, s | 166.6 s | 165.8 s | 166.0 s | 166.9 s | 164.0 s | 164.7 s |
| 3 | 60.0 d | 59.0 d | 59.7 d | 79.8, d | 59.7 d | 60.0 d | 59.7 d | 60.2 d | 59.1 d | 60.1 d |
| 5 | 46.5 t | 45.8 t | 46.7 t | 63.3, t | 46.6 t | 46.6 t | 46.6 t | 47.2 t | 45.8 t | 46.4 t |
| 6 | 42.7 t | 41.8 t | 42.9 t | 43.7, t | 43.1 t | 42.7 t | 42.9 t | 43.2 t | 41.8 t | 42.5 t |
| 7 | 55.2 s | 55.3 s | 55.6 s | 53.4, s | 55.6 s | 55.3 s | 55.9 s | 56.6 s | 54.4 s | 55.3 s |
| 8 | 138.9 s | 139.0 s | 130.5 s | 133.9, s | 130.5 s | 133.1 s | 134.5 s | 135.0 s | 138.1 s | 138.8 s |
| 9 | 122.0 d | 121.1 d | 110.1 d | 104.0, d | 110.1 d | 112.9 d | 105.8 d | 107.0 d | 121.1 d | 123.1 d |
| 10 | 120.6 d | 119.7 d | 141.2 s | 146.9, s | 141.3 s | 104.3 d | 145.7 s | 146.3 s | 119.8 d | 121.3 d |
| 11 | 128.5 d | 127.7 d | 147.5 s | 141.8, s | 147.6 s | 148.7 s | 140.3 s | 141.3 s | 127.6 d | 128.2 d |
| 12 | 110.4 d | 109.6 d | 96.1 d | 139.7, s | 96.1 d | 131.5 s | 137.9 s | 138.5 s | 109.5 d | 110.0 d |
| 13 | 144.7 s | 144.8 s | 136.9 d | 130.0, s | 136.8 s | 132.0 s | 128.9 s | 129.2 s | 143.8 s | 144.4 s |
| 14 | 86.3 d | 85.6 d | 86.5 d | 90.2, d | 86.7 d | 86.4 d | 86.6 d | 86.9 d | 85.6 d | 86.2 d |
| 15 | 69.9 d | 69.0 d | 69.8 d | 68.7, d | 69.8 d | 69.9 d | 69.7 d | 70.3 d | 69.0 d | 70.0 d |
| 16 | 91.5 s | 90.9 s | 91.4 s | 96.6, s | 90.3 s | 91.2 s | 91.0 s | 91.3 s | 90.6 s | 91.2 s |
| 17 | 23.4 t | 23.4 t | 23.3 t | 25.7, t | 23.2 t | 23.2 t | 22.9 t | 23.4 t | 22.5 t | 23.4 t |
| 18 | 7.6 q | 6.8 q | 7.6 q | 8.0, q | 7.3 q | 7.7 q | 7.5 q | 7.6 q | 6.8 q | 7.7 q |
| 19 | 27.6 t | 27.6 t | 27.7 t | 29.5, t | 27.7 t | 27.6 t | 27.7 t | 28.2 t | 26.7 t | 27.5 t |
| 20 | 45.6 s | 45.4 s | 45.4 s | 45.4, s | 45.5 s | 45.8 s | 45.6 s | 45.9 s | 44.7 s | 46.4 s |
| 21 | 66.2 d | 65.4 d | 66.1 d | 76.2, d | 66.1 d | 66.4 d | 66.1 d | 66.6 d | 65.4 d | 66.3 d |
| COOCH₃ | 168.5 s | 168.1 s | 168.7 s | 170.0, s | 168.6 s | 168.5 s | 169.1 s | 169.1 s | 167.2 s | 168.2 s |
| COOCH₃ | 50.9 q | 50.3 q | 50.7 q | 52.0, q | 50.5 q | 51.1 q | 50.9 q | 51.4 q | 50.3 q | 51.0 q |
| 11-OCH₃ | | | 56.5 q | 62.1, q | 56.5 q | 56.6 q | | 61.0 q | | 61.2 q |
| 12-OCH₃ | | | | 61.6, q | | | 60.7 q | 61.0 q | | |
| 2' | 166.2 s | 166.7 s | 166.1 s | 165.9, s | 168.2 s | 168.3 s | 168.1 s | 164.5 s | 165.7 s | 168.0 s |
| 3' | 50.0 t | 164.4 s | 49.7 t | 50.7, t | 50.8 t | 50.5 t | 50.5 t | 172.0 s | 160.1 s | 161.1 s |
| 5' | 51.4 t | 42.9 t | 51.4 t | 52.2, t | 50.9 t | 50.9 t | 50.8 t | 44.2 t | 42.7 t | 42.4 t |
| 6' | 45.6 t | 42.3 t | 45.5 t | 46.6, t | 46.4 t | 46.2 t | 46.3 t | 41.1 t | 43.8 t | 46.3 t |
| 7' | 55.2 s | 58.1 s | 55.4 s | 56.0, s | 55.6 s | 55.6 s | 55.6 s | 57.7 s | 56.6 s | 63.5 s |
| 8' | 131.4 d | 129.2 s | 131.6 s | 133.8, s | 131.3 s | 131.2 s | 131.3 s | 130.1 s | 128.6 s | 126.3 s |
| 9' | 120.4 s | 120.0 s | 120.5 d | 123.4, d | 120.3 d | 120.3 d | 120.3 d | 120.0 d | 120.0 d | 124.6 d |
| 10' | 115.2 s | 115.2 s | 115.7 s | 112.3, s | 115.6 s | 115.4 s | 115.4 s | 116.6 s | 115.1 s | 115.8 s |
| 11' | 161.7 s | 162.1 s | 161.5 s | 163.5, s | 161.6 s | 161.7 s | 161.5 s | 162.4 s | 161.2 s | 161.5 s |
| 12' | 93.6 d | 93.1 s | 93.7 d | 95.0, d | 93.9 d | 93.7 d | 93.9 d | 94.0 d | 93.0 d | 93.1 d |
| 13' | 146.2 s | 146.2 s | 146.0 s | 149.7, s | 145.9 s | 146.2 s | 145.9 s | 146.9 s | 145.3 s | 146.0 s |
| 14' | 52.4 d | 51.1 d | 52.3 d | 53.2, d | 54.2 d | 54.6 d | 54.2 d | 41.0 t | 122.8 d | 122.3 d |
| 15' | 56.0 d | 56.7 d | 56.2 d | 57.1, d | 57.4 d | 57.2 d | 57.4 d | 70.3 d | 145.5 d | 145.0 d |
| 16' | 91.5 s | 88.8 s | 90.3 s | 93.9, s | 91.0 s | 91.8 s | 91.3 s | 91.5 s | 90.0 s | 89.1 s |
| 17' | 24.0 t | 22.8 s | 24.4 t | 25.6, t | 24.2 t | 24.0 t | 24.1 t | 23.1 t | 25.4 t | 23.6 t |
| 18' | 7.7 q | 6.7 q | 7.4 q | 8.5, q | 7.5 q | 7.9 q | 7.4 q | 8.2 q | 6.7 q | 7.6 q |
| 19' | 27.2 t | 27.6 t | 27.3 t | 28.3, t | 25.3 t | 27.2 t | 25.3 t | 28.5 t | 27.3 t | 28.2 t |
| 20' | 38.2 s | 40.6 s | 37.7 s | 38.8, s | 41.8 s | 42.2 s | 41.8 s | 45.3 s | 40.3 s | 45.6 s |
| 21' | 72.4 d | 64.3 d | 72.0 d | 72.4, d | 68.7 d | 69.1 d | 68.6 d | 70.6 d | 67.3 d | 96.9 s |
| COOCH₃ | 168.5 s | 167.4 s | 168.6 s | 170.0, s | 168.7 s | 168.6 s | 168.6 s | 169.8 s | 167.9 s | 168.6 s |
| COOCH₃ | 51.0 q | 50.0 q | 50.9 q | 52.0, q | 50.7 q | 51.1 q | 50.7 q | 51.5 q | 50.0 q | 51.0 q |

[a] recorded at 150 MHz,
[b] at 200 MHz.

TABLE 3

Data attribution of ¹H NMR of compounds 11-16 (acetone-d₆)

| No. | $\delta_H$ 11[a] | $\delta_H$ 12[b] | $\delta_H$ 13[c] | $\delta_H$ 14[c] | $\delta_H$ 15[c] | $\delta_H$ 16[c] |
|---|---|---|---|---|---|---|
| NH | 9.27, s | 8.87, s | 8.87, s | 9.07, s | 9.01, s | 8.78, s |
| 3 | 4.94, d, 7.8 | 4.89, d, 7.9 | 4.89, d, 7.9 | 4.85, d, 7.6 | 4.84, d, 7.2 | 4.90, d, 7.8 |
| 5 | 3.03, overlap | 3.00, overlap | 2.98, m | 2.80, overlap | 2.78, overlap | 2.94, ddd, 12.5, 8.6, 4.3 |
|   | 2.99, overlap | 2.90, m | 2.91, m | 3.00, overlap | 3.00, overlap | 3.03, dd, 8.6, 6.1 |
| 6 | 1.99, m | 1.95, m | 1.94, overlap | 1.55, dd, 11.6, 4.2 | 1.59, dd, 11.3, 4.5 | 1.58, dd, 11.2, 4.3 |
|   | 1.56, dd, 11.5, 4.5 | 1.55, dd, 11.3, 4.2 | 1.54, dd, 11.2, 4.2 | 1.95, td, 11.6, 6.2 | 1.95, td, 11.3, 6.1 | 1.96, overlap |
| 9 | 6.15, d, 7.5 | 5.80, d, 8.1 | 5.62, d, 8.1 | 5.82, s | 5.89, s | 5.66, s |
| 10 | 6.44, td, 7.5, 1.1 | 5.98, d, 8.1 | 5.96, d, 8.1 | | | |
| 12 | 7.03, td, 7.5, 1.1 | | | 6.69, s | 6.72, s | |
| 14 | 6.96, d, 7.5 | 4.98, dd, 7.9, 3.5 | 4.98, dd, 7.9, 3.5 | 4.94, dd, 7.6, 3.5) | 4.92, dd, 7.2, 3.7 | 4.99, dd, 7.8, 3.6 |
| 15 | 5.02, dd, 7.8, 3.6 | 4.07, dd, 10.5, 3.5 | 4.07, dd, 10.8, 3.5 | 4.10, dd, 9.6, 3.5 | 4.12, dd, 9.0, 3.7 | 4.11, overlap |
| 17 | 4.10, dd, 10.4, 3.6 | 2.64, d, 15.2 | 2.63, d, 15.4 | 2.49, d, 15.6 | 2.54, d, 15.4 | 2.55, d, 15.4 |
|   | | 2.51, d, 15.2 | 2.53, d, 15.4 | 2.67, dd, 15.6, 2.0 | 2.68, dd, 15.4, 2.0 | 2.65, overlap |
| 18 | 2.70, d, 15.2 | 0.67, t, 7.2 | 0.67, t, 7.3 | 0.68, t, 7.2 | 0.67, t, 7.3 | 0.69, t, 7.2 |
|   | 2.56, d, 15.2 | | | | | |

TABLE 3-continued

Data attribution of $^1$H NMR of compounds 11-16 (acetone-$d_6$)

| No. | $\delta_H$ 11[a] | $\delta_H$ 12[b] | $\delta_H$ 13[c] | $\delta_H$ 14[c] | $\delta_H$ 15[c] | $\delta_H$ 16[c] |
|---|---|---|---|---|---|---|
| 19 | 0.69, t, 7.3 | 1.30, m | 1.09, m | 0.81, m | 0.78, m | 0.78, m |
|  | 1.09, m | 0.75, m | 1.07, m | 1.04, m | 1.09, m |
| 21 | 0.77, m | 2.48, s | 2.49, br s | 2.56, br s | 2.66, br s | 2.56, d, 1.8 |
|  | 1.10, m |  |  |  |  |  |
| COOCH$_3$ | 2.54, s | 3.72, s | 3.72, s | 3.70, s | 3.72, s | 3.73, s |
| 11-OCH$_3$ | 3.73, s | 3.70, s | 3.68, s | 3.75, s | 3.37, s | 3.71, s |
| 12-OCH$_3$ |  | 3.79, s |  |  | 3.71, s | 3.87, s |
| NH' | 9.56 | 9.39, s | 9.40, s | 9.39 s | 9.41, s | 9.58, s |
| 3' | 4.47, m | 3.44, dd, 16.2, 4.2 | 3.44, dd, 16.1, 3.7 | 3.23, d, 15.9 | 3.24, dt, 15.9, 2.0 |  |
|  | 3.36, m | 3.22, d, 16.2 | 3.21, d, 16.1 | 3.43, dd, 15.9, 2.1 | 3.43, ddd, 15.9, 4.7, 1.5 |  |
| 5' |  | 3.03, overlap | 3.02, m | 2.79, m | 2.80, overlap | 3.41, td, 12.2, 5.0 |
|  |  | 2.81, overlap | 2.80, m | 3.02, overlap | 3.02, overlap | 4.20, dd, 12.2, 7.1 |
| 6' | 2.79, overlap | 2.02, m | 2.02, m | 1.74, dd, 11.4, 4.5 | 1.74, ddd, 11.5, 4.9, 1.4 | 1.83, dd, 12.1, 5.0 |
|  | 2.53, overlap | 1.75, dd, 11.5, 4.4 | 1.75, dd, 11.2, 4.3 | 2.01, m | 20.3, m | 1.98, overlap |
| 9' | 7.49, s | 7.44, s | 7.43, s | 7.42, s | 7.42, s | 7.66, s |
| 12' | 6.62, s | 6.58, s | 6.57, s | 6.59, s | 6.65, s | 6.66, s |
| 14' | 5.85, ddd, 10.3 4.2, 1.7 | 5.79, d, 3.8 | 5.78, overlap | 5.76, overlap | 5.80, ddd, 10.0, 4.7, 1.5 | 5.82, d, 10.1 |
| 15' | 5.92, overlap | 5.80, d, 3.8 | 5.81, overlap | 5.76, overlap | 5.75, dt, 10.0, 2.0 | 6.58, d, 10.1 |
| 17' | 1.99, overlap | 2.63, d, 14.7 | 2.60, d, 14.7 | 2.43, d, 15.0 | 2.46, d, 14.9 | 2.04, overlap |
|  | 2.73, overlap | 2.53, d, 14.7 | 2.48, d, 14.7 | 2.58, d, 15.0 | 2.59, dd, 14.9, 1.9 | 2.65, overlap |
| 18' | 0.88, t, 7.4 | 0.86, t, 7.4 | 0.86, t, 7.4 | 0.72, t, 7.4 | 0.72, t, 7.4 | 0.78, t, 7.4 |
| 19' | 1.37, m | 1.03, m | 1.30, m | 1.14, m | 1.07, m | 1.28, m |
|  | 1.31, m | 0.75, m | 1.05, m | 1.22, m | 1.21, m |  |
| 21' | 4.04, s | 2.78, s | 2.78, br s | 2.80, overlap | 2.86, overlap | 4.12, br s |
| COOCH$_3$ | 3.71, s | 3.70, s | 3.70, s | 3.70, s | 3.70, s | 3.73, s |

[a]recorded at 800 MHz;
[b]at 500 MHz,
[c]at 600 MHz.

TABLE 4

Data attribution of $^{13}$C NMR of compounds 11-16 (acetone-$d_6$).

| No. | $\delta_C$ 11[a] | $\delta_C$ 12[b] | $\delta_C$ 13[c] | $\delta_C$ 14[c] | $\delta_C$ 15[c] | $\delta_C$ 16[c] |
|---|---|---|---|---|---|---|
| 2 | 164.7 s | 165.7 s | 165.3 s | 166.7 s | 167.2 s | 166.0 s |
| 3 | 58.9 d | 59.9 d | 59.9 d | 59.8 d | 60.0 d | 59.8 d |
| 5 | 45.7 s | 46.4 t | 46.5 t | 46.7 t | 46.5 t | 46.9 t |
| 6 | 41.8 t | 42.6 t | 42.6 t | 43.2 t | 43.1 t | 42.8 t |
| 7 | 55.2 s | 55.2 s | 55.1 s | 55.2 s | 55.2 s | 56.1 s |
| 8 | 138.9 s | 132.9 s | 132.8 s | 130.6 s | 130.1 s | 134.7 s |
| 9 | 121.1 d | 112.8 d | 116.9 d | 110.2 d | 112.6 d | 106.2 d |
| 10 | 119.8 d | 104.2 d | 104.8 d | 141.3 s | 144.3 s | 145.8 s |
| 11 | 127.6 d | 148.6 s | 153.3 s | 147.6 s | 151.7 s | 140.5 s |
| 12 | 109.6 d | 131.9 s | 133.7 s | 96.1 d | 97.0 d | 138.1 s |
| 13 | 144.6 s | 131.4 s | 137.3 s | 137.0 s | 139.7 s | 129.1 s |
| 14 | 85.7 d | 86.3 d | 86.7 d | 86.8 d | 86.8 d | 86.7 d |
| 15 | 69.0 d | 69.8 d | 69.8 d | 70.4 d | 70.1 d | 69.8 d |
| 16 | 92.0 s | 91.7 s | 93.5 s | 90.5 s | 91.4 s | 91.5 s |
| 17 | 23.3 t | 23.1 t | 28.3 t | 23.3 t | 23.3 t | 23.2 t |
| 18 | 7.7 q | 7.6 q | 7.6 q | 7.7 q | 7.6 q | 7.7 q |
| 19 | 27.6 t | 27.5 t | 27.5 t | 27.5 t | 28.0 t | 27.9 t |
| 20 | 45.5 s | 45.7 s | 45.7 s | 45.5 s | 45.3 s | 45.7 s |
| 21 | 65.4 d | 66.3 d | 66.3 d | 66.2 d | 66.4 d | 66.4 d |
| COOCH$_3$ | 169.8 s | 169.0 s | 169.0 s | 168.8 s | 168.7 s | 169.2 s |
| COOCH$_3$ | 51.4 q | 50.9 q | 50.9 q | 50.8 q | 51.0 q | 51.1 q |
| 11-OCH$_3$ |  | 56.4 q | 56.2 q | 56.5 q | 59.5 q | 61.1 q |
| 12-OCH$_3$ |  | 60.7 q |  |  | 56.3 q | 60.8 q |
| 2' | 165.5 s | 167.4 s | 167.4 s | 167.6 s | 167.2 s | 166.6 s |
| 3' | 39.3 t | 51.0 t | 51.1 t | 51.0 t | 50.8 t | 161.3 s |
| 5' | 169.0 t | 51.1, t | 51.0 t | 51.3 t | 51.2 t | 43.7 t |
| 6' | 47.4 t | 45.9 t | 45.9 t | 46.1 t | 46.0 t | 44.8 t |
| 7' | 49.3 s | 55.6 s | 55.6 s | 55.9 s | 55.9 s | 57.6 s |
| 8' | 130.2 s | 131.5 s | 131.5 s | 131.8 s | 131.5 s | 129.7 s |
| 9' | 119.3 d | 120.4 d | 120.3 d | 120.5 d | 120.3 d | 120.9 d |
| 10' | 116.5 s | 115.2 s | 115.1 s | 115.7 s | 115.8 s | 116.3 s |
| 11' | 162.0 s | 161.6 s | 161.6 s | 161.6 s | 161.5 s | 162.1 s |
| 12' | 92.9 d | 93.5 d | 93.5 d | 93.9 d | 93.8 d | 94.2 d |
| 13' | 146.4 s | 146.2 s | 146.2 s | 146.2 s | 146.2 s | 146.2 s |
| 14' | 123.0 d | 126.0 d | 126.0 d | 125.6 d | 125.8 d | 123.4 d |
| 15' | 131.3 d | 133.0 d | 133.0 d | 133.8 d | 133.7 d | 146.0 d |
| 16' | 90.4 s | 92.3 s | 92.3 s | 92.4 s | 92.4 s | 90.7 s |
| 17' | 28.7 t | 28.3 t | 23.1 t | 29.2 t | 29.9 t | 26.4 t |
| 18' | 7.3 q | 7.9 q | 7.9 q | 7.8 q | 7.9 q | 7.4 q |
| 19' | 29.0 t | 27.5 t | 27.5 t | 27.9 t | 27.9 t | 28.0 t |
| 20' | 39.3 s | 42.3 s | 42.3 s | 42.0 s | 41.8 s | 41.5 s |
| 21' | 66.4 d | 71.9 d | 71.9 d | 70.0 d | 70.4 d | 68.3 d |
| COOCH$_3$ | 168.5 s | 168.5 s | 168.5 s | 168.8 s | 168.6 s | 168.2 s |
| COOCH$_3$ | 51.0 q | 50.9 q | 51.0 q | 50.8 q | 50.9 q | 51.2 q |

[a]recorded at 200 MHz;
[b]at 125 MHz;
[c]at 150 MHz.

TABLE 5

Data attribution of $^{13}$C NMR of taberyunine A, taberyunine C, conophylline, conophyllinine and conophyllidine (acetone-d$_6$)

| No. | $\delta_C{}^a$ (taberyunine A) | $\delta_C{}^a$ (taberyunine C) | $\delta_C{}^b$ (conophylline) | $\delta_C{}^c$ (conophyllinine) | $\delta_C{}^b$ (conophyllidine) |
|---|---|---|---|---|---|
| 2 | 165.2 s | 165.8 s | 165.8 s | 166.3 s | 166.1 s |
| 3 | 59.9 d | 60.0 d | 59.7 d | 59.7 d | 59.7 d |
| 5 | 46.5 t | 46.5 t | 51.4 t | 46.7 t | 51.2 t |
| 6 | 42.7 t | 42.7 t | 42.8 t | 43.0 t | 42.9 t |
| 7 | 54.6 s | 55.2 s | 55.3 s | 55.9 s | 55.8 s |
| 8 | 131.3 s | 133.1 s | 134.6 s | 134.5 s | 134.6 s |
| 9 | 122.2 d | 112.9 d | 106.0 d | 106.1 d | 106.0 d |
| 10 | 105.0 d | 104.2 d | 145.7 s | 145.6 s | 145.7 s |
| 11 | 160.9 s | 148.7 s | 140.3 s | 140.3 s | 140.3 s |
| 12 | 97.7 s | 132.1 s | 138.0 s | 137.9 s | 137.9 s |
| 13 | 145.8 s | 146.3 s | 128.9 s | 128.9 s | 128.9 s |
| 14 | 86.3 d | 86.4 d | 86.5 d | 86.7 d | 86.6 d |
| 15 | 69.8 d | 69.8 d | 69.7 d | 70.3 d | 69.8 d |
| 16 | 91.5 s | 91.8 s | 91.4 s | 91.7 s | 91.4 s |
| 17 | 23.3 t | 23.2 t | 23.0 t | 23.3 t | 23.0 t |
| 18 | 7.6 q | 7.7 q | 7.6 q | 7.5 t | 7.6 q |
| 19 | 27.5 t | 27.6 t | 27.8 t | 27.7 t | 27.8 t |
| 20 | 45.6 s | 45.8 s | 45.5 s | 45.4 s | 45.5 s |
| 21 | 66.3 d | 66.4 d | 66.2 d | 66.1 d | 66.2 d |
| COOCH$_3$ | 168.5 s | 169.1 s | 168.6 s | 169.1 s | 168.7 s |
| COOCH$_3$ | 51.0 q | 51.1 q | 50.9 q | 50.9 q | 50.9 q |
| 11-OCH$_3$ | 55.6 q | 56.5 q | 61.0 q | 61.1 q | 61.0 q |
| 12-OCH$_3$ |  |  | 60.7 q | 60.7 q | 60.7 q |
| 2' | 166.2 s | 166.3 s | 166.1 s | 168.5 s | 167.4 s |
| 3' | 50.0 t | 50.1 t | 49.7 t | 55.3 t | 50.9 t |
| 5' | 51.3 t | 51.4 t | 46.7 t | 51.2 t | 46.6 t |
| 6' | 45.5 t | 45.8 t | 45.5 t | 45.4 t | 46.0 t |
| 7' | 55.3 s | 55.2 s | 55.1 s | 56.1 s | 55.9 s |
| 8' | 131.3 d | 131.4 d | 131.6 s | 130 8 s | 131.7 s |
| 9' | 120.4 s | 120.6 s | 120.5 d | 119.8 d | 120.4 d |
| 10' | 115 2 d | 115.3 d | 115.5 s | 115.5 s | 115.4 d |
| 11' | 16 1.5 s | 161.7 s | 161.5 s | 161.4 s | 161.5 s |
| 12' | 93.5 d | 93.6 d | 93.7 s | 94.0 d | 93.7 d |
| 13' | 146.2 s | 146.2 s | 146.1 s | 146.3 s | 146.2 s |
| 14' | 52.4 d | 52.5 d | 52.5 d | 86.7 d | 125.6 d |
| 15' | 56.0 d | 56.0 d | 56.9 d | 80.8 d | 133.8 d |
| 16' | 91.6 s | 91.5 s | 91.3 s | 92.3 s | 91.4 s |
| 17' | 23.8 t | 2.38 t | 23.0 t | 23.0 t | 2.30 t |
| 18' | 7.8 q | 7.9 q | 7.4 q | 9.0 q | 7.6 q |
| 19' | 27.1 t | 27.1 t | 27.4 t | 27.8 t | 27.8 t |
| 20' | 38.2 s | 38.4 s | 37.7 s | 44.2 s | 41.9 s |
| 21' | 72.6 d | 72.7 d | 72.0 d | 70.6 d | 71.2 d |
| COOCH$_3$ | 168.6 s | 168.7 s | 169.1 s | 169.1 s | 169.1 s |
| COOCH$_3$ | 51.0 q | 51.1 q | 50.9 q | 50.8 q | 50.9 q |

$^a$recorded at 150 MHz;
$^b$at 100 MHz;
$^c$at 125 MHz

TABLE 6

Data attribution of $^{13}$C NMR of Melodinine K, 19'-hydroxy-melodinine K, 3'-acetonyl-melodinine K and taberyunine B (acetone-d$_6$)

| No. | $\delta_C{}^a$ (melodinine K) | $\delta_C{}^b$ (19'-hydroxy-melodinine K) | $\delta_C{}^a$ (3'-acetonyl-melodinine K) | $\delta_C{}^a$ (taberyunine B) |
|---|---|---|---|---|
| 2 | 164.9 | 165.5 s | 164.9 s | 165,1 s |
| 3 | 60.0 | 59.6 d | 60.1 d | 59.9 d |
| 5 | 45.6 | 51.4 t | 46.8 t | 46.5 t |
| 6 | 42.8 | 43.2 t | 42.7 t | 42.8 t |
| 7 | 55.2 | 55.2 s | 55.3 s | 54.6 s |
| 8 | 139.0 | 139.0 s | 139.1 s | 131.2 s |
| 9 | 122.1 | 122.1 d | 122.2 d | 122.3 d |
| 10 | 120.7 | 110.3 d | 120.9 d | 105.0 d |
| 11 | 128.5 | 128.4 d | 128.2 s | 160.9 s |
| 12 | 110.4 | 121.2 d | 101.4 d | 97.6 d |
| 13 | 146.2 | 144.6 s | 144.7 s | 145.9 s |
| 14 | 86.4 | 86.7 d | 86.4 d | 86.3 d |
| 15 | 69.8 | 70.0 d | 70.0 d | 69.8 d |
| 16 | 91.5 | 91.7 s | 91.1 s | 92.5 s |

TABLE 6-continued

Data attribution of $^{13}$C NMR of Melodinine K, 19'-hydroxy-melodinine K, 3'-acetonyl-melodinine K and taberyunine B (acetone-$d_6$)

| No. | $\delta_C{}^a$ (melodinine K) | $\delta_C{}^b$ (19'-hydroxy-melodinine K) | $\delta_C{}^a$ (3'-acetonyl-melodinine K) | $\delta_C{}^a$ (taberyunine B) |
|---|---|---|---|---|
| 17 | 23.4 | 23.4 t | 23.5 t | 23.3 t |
| 18 | 7.7 | 7.5 q | 7.7 q | 7.6 q |
| 19 | 27.7 | 27.8 t | 31.3 t | 27.5 t |
| 20 | 46.6 | 40.2 s | 45.6 s | 45.6 s |
| 21 | 66.3 | 66.3 d | 65.4 d | 66.3 d |
| COOCH$_3$ | 167.6 | 169.0 s | 168.7 s | 168.6 s |
| $\overline{C}$OOCH$_3$ | 51.0 | 51.0 q | 51.0 q | 51.0 q |
| 11-O$\overline{C}$H$_3$ |  |  |  | 55.5 q |
| 2' | 164.8 | 166.8 s | 166.5 s | 166.5 s |
| 3' | 51.2 | 51.1 t | 53.2 d | 51.1 t |
| 5' | 51.2 | 46.5 t | 52.4 t | 51.2 t |
| 6' | 46.1 | 46.2 t | 43.8 t | 46.0 t |
| 7' | 55.7 | 55.8 s | 56.4 s | 55.6 s |
| 8' | 131.2 | 131.1 s | 132.8 s | 131.5 s |
| 9' | 120.4 | 120.1 d | 120.7 d | 120.3 d |
| 10' | 115.3 | 115.2 s | 115.1 s | 115.2 s |
| 11' | 161.7 | 161.6 s | 161.6 s | 161.6 s |
| 12' | 93.7 | 92.8 d | 93.3 d | 93.6 d |
| 13' | 144.7 | 146.5 s | 145.7 s | 146.2 s |
| 14' | 126.2 | 126.7 d | 128.6 d | 126.0 d |
| 15' | 133.2 | 131.1 d | 132.6 d | 133.0 d |
| 16' | 92.5 | 92.8 s | 91.5 s | 91.7 s |
| 17' | 28.5 | 28.5 t | 27.6 t | 28.3 t |
| 18' | 7.9 | 19.5 q | 8.4 q | 7.9 q |
| 19' | 27.7 | 66.3 d | 31.7 t | 27.5 t |
| 20' | 42.4 | 47.5 s | 37.9 s | 42.3 s |
| 21' | 71.8 | 67.2 d | 67.1 d | 71.6 d |
| COOCH$_3$ | 168.7 | 168.7 s | 168.7 s | 168.0 s |
| $\overline{C}$OOCH$_3$ | 51.1 | 50.8 q | 51.0 q | 50.9 q |
| CH$_2\overline{C}$OCH$_3$ |  |  | 47.0 t |  |
| CH$_2$COCH$_3$ |  |  | 206.9 s |  |
| CH$_2\overline{C}$OCH$_3$ |  |  | 30.7 q |  |

[a] recorded on 150 MHz;
[b] recorded on 100 MHz.

TEST EXAMPLE

Figure 2:
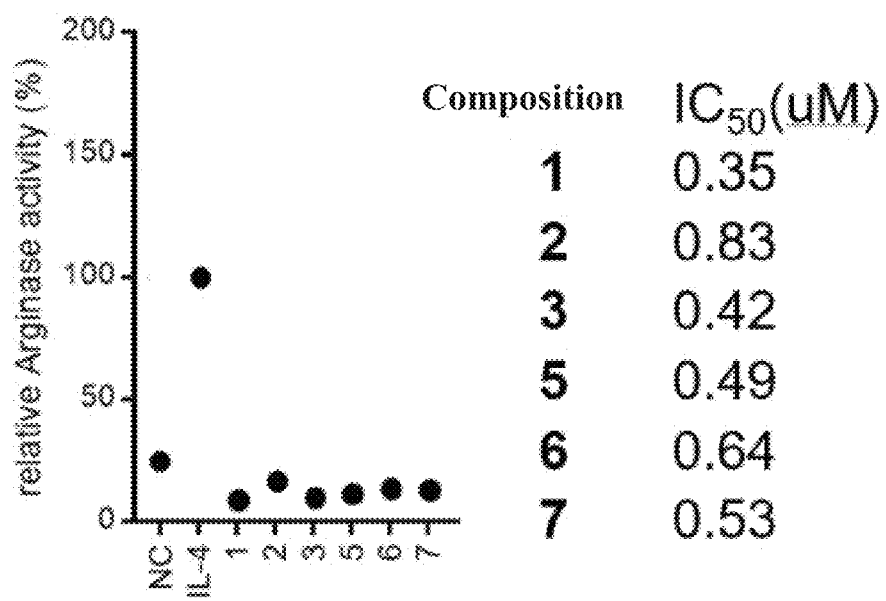
FIG. 2 shows a data graph of the activated immune assay of compounds 1-3 and 5-7.

Activated immune test: bone marrow-derived macrophages (BMMs), as primary cells isolated from bone marrow and subjected to induced culture that can well reflect functions of the macrophages, are commonly used cells to study the functions of the macrophages. A mouse femur bone marrow was isolated and cultured in a medium containing an mCSF factor for 6-7 d to obtain mature BMMs; stimulation with IL-4 for 12 h can induce polarization of the BMMs to an immunosuppressive M2 type with high expression of ARG1; after the ARG1 protein was extracted, arginine hydrolysis was conducted in vitro, and color development was further conducted by reacting α-isonitrosopropiophenone with a hydrolyzate urea; an absorbance was measured at a wavelength of 540 nm as a marker of an ARG1 activity. A specific process was as follows: cells were pretreated with drugs (1 μM) (including the CPLD, CPLL, TBYA, MDK, HMD, compounds 1-3 and compounds 5-7); IL-4 stimulation was conducted for 12 h, followed by washing with PBS, and cells were lysed with a lysis buffer containing a protease inhibitor, and a total cell protein was obtained; after adding 0.2 nM to 0.4 mM Mn$^2$, the total cell protein was heated at 55° C. for 10 min to fully activate an arginase ARG1. 0.5 mM arginine was added for incubation at 37° C. for 1 h to 2 h to fully hydrolyze the arginine. An acid solution containing sulfuric acid and phosphoric acid was added to stop the reaction, a 9% α-isonitrosopropiophenone ethanol solution was added, followed by heating at 95° C. for 15 min to 30 min to develop color. The experimental results are shown in FIG. 1. It can be seen from FIG. 1 that the compounds CPLD, CPLL, TBYA, MDK and HMD can significantly inhibit the expression of arginase induced by IL-4 in macrophages and inhibit the M2 polarization of the macrophages; it can also be seen from FIG. 1 that (where A is the inhibition of macrophage M2 polarization, B is the structural formulas of CPLD, CPLL, TBYA, MDK and HMD, and C is the concentration-dependent relationship of the compounds): the CPLD, CPLL, TBYA, MDK and HMD can significantly inhibit IL-4-induced arginase expression in the macrophages and inhibit M2 polarization of the macrophages in a concentration-dependent manner. It can be seen from FIG. 2 that the compounds 1-3 and 5-7 can also inhibit the M2 polarization of macrophages in a concentration-dependent manner.

Figure 3:
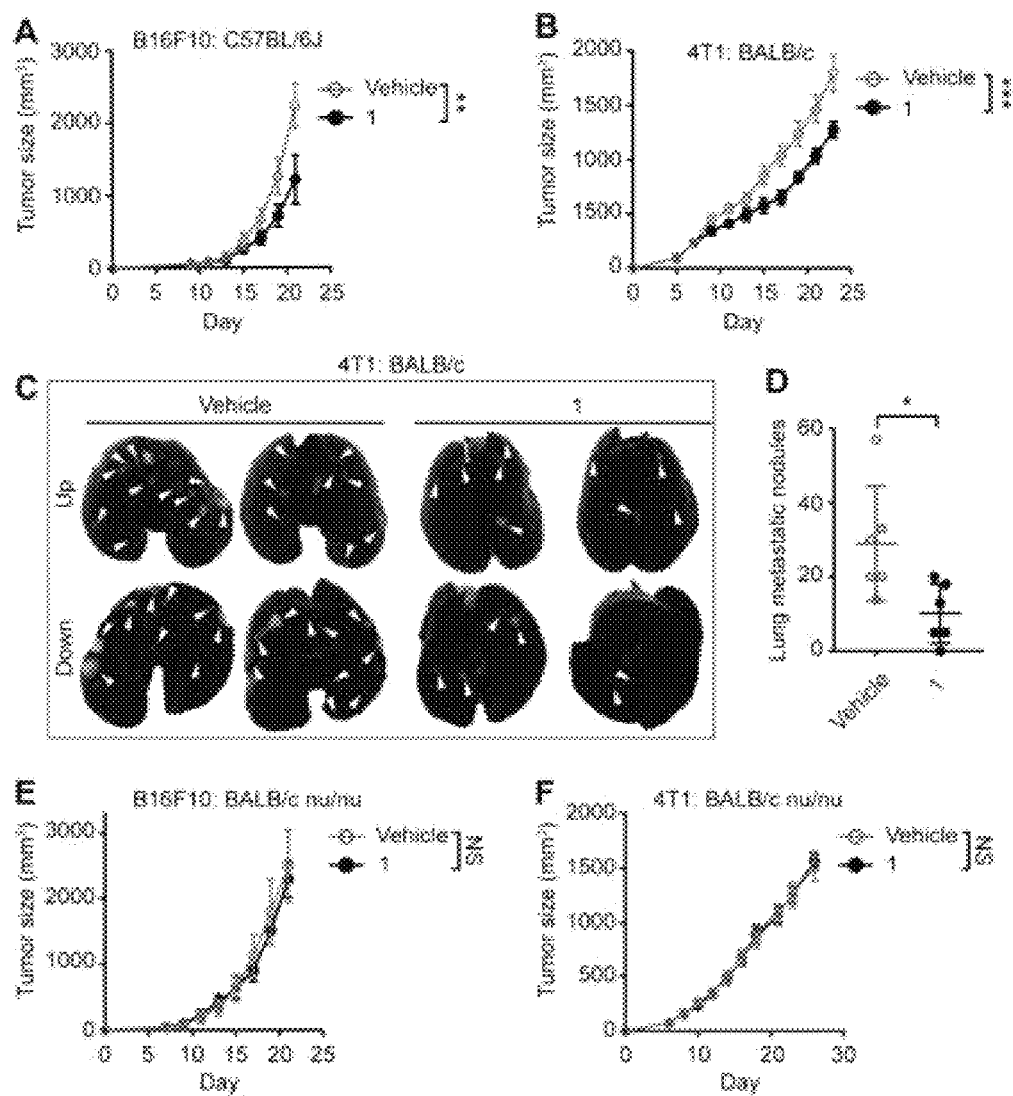
FIG. 3 shows a data graph of an in vivo activated immune activity of the compound 1.

Validation of immune-dependent activity: in a mouse melanoma model, the compound 1 was administered intraperitoneally for 4 times at a dosage of 2 mg/kg. The test results are shown in FIG. 3. The compound 1 has obvious anti-tumor effect, and its anti-tumor activity depends on the immune system; in a normal mouse melanoma model (A) and a breast cancer model (B), the compound 1 significantly inhibits tumor growth and inhibits spontaneous lung metastasis of breast cancer (C and D); in a melanoma model (E) and a breast cancer cell model (F) constructed using Balb/c nude mice, an antitumor activity of the compound 1 disappears.

Figure 4:
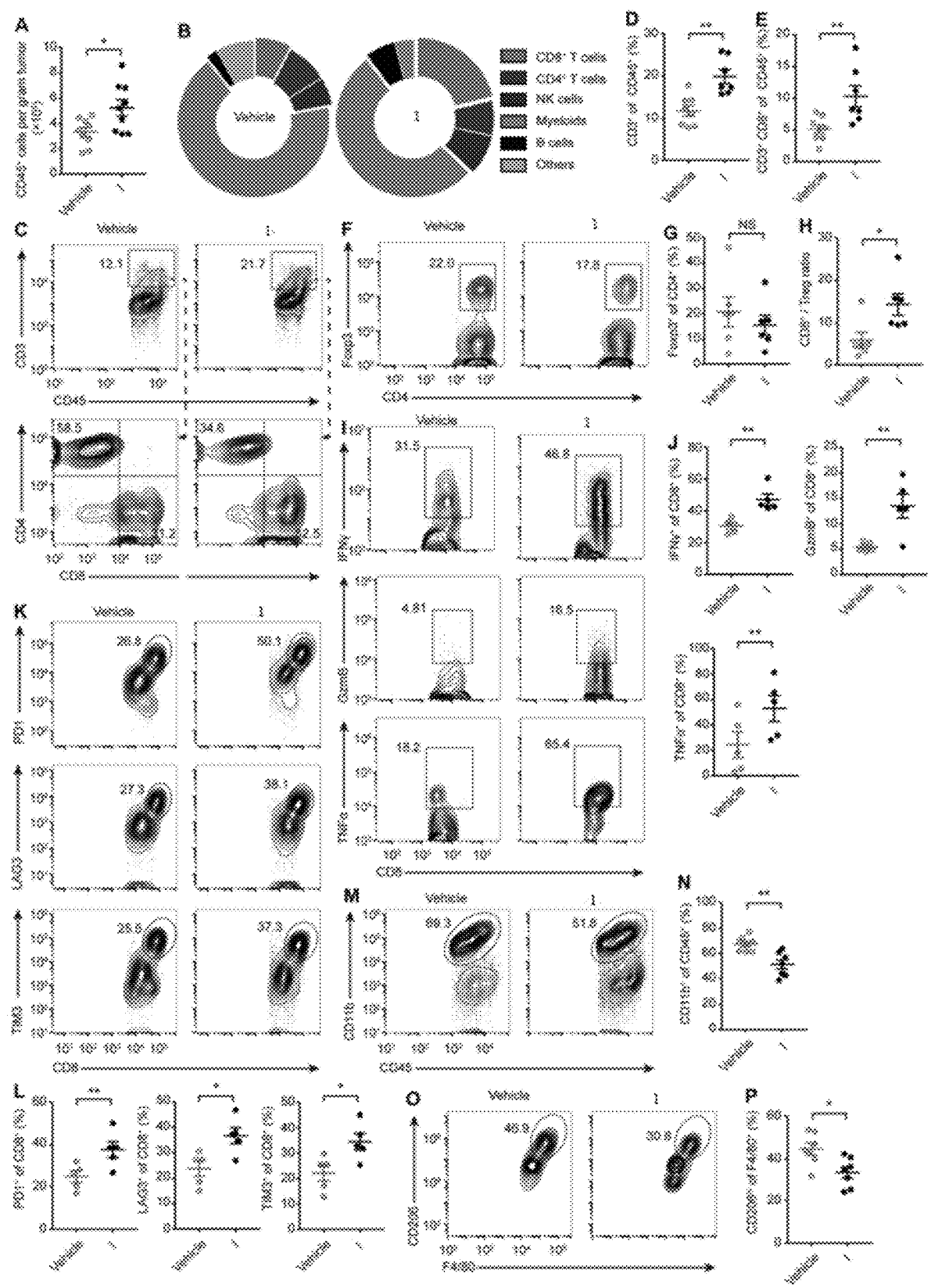
FIG. 4 shows a data graph that the compound 1 improves and enhances a $CD8^+$ T cell function.

Validation of improving and enhancing CD8$^+$ T cell function: through FACS analysis, the test results of compound 1 are shown in FIG. 3. The compound 1 can promote infiltration of immune cells in the tumors, up-regulate a proportion of the CD8 T cells and down-regulate a proportion of myeloid cells, but has no significant effect on CD4 T cells, Treg cells, NK cells and B cells. Further researches have found that the compound 1 can promote a function of the CD8$^+$ T cells, enhance IFNγ, Granzyme B and TNFα, and up-regulate PD1, LAG3 and TIM3. In addition, the compound 1 is able to down-regulate a proportion of CD206$^+$ macrophages (FIG. 4). (A) shows that the compound 1 can activate tumor immune response; (B) regulates a proportion of immune cell populations in the microenvironment; (C-E) can up-regulate a proportion of T cells, especially CD8$^+$ T cells; (F-H) have no significant effect on a Treg ratio; (I, J) can promote the function of CD8 T cells and up-regulate expression of IFNγ, Granzyme B and TNFα; (K, L) can simultaneously up-regulate expressions of the PD1, LAG3 and TIM3; (M, N) can down-regulate a proportion of the myeloid cells (CD11b$^+$) in the tumor microenvironment; and (0, P) affects especially a proportion of M2-type TAMs (CD206$^{hi}$). *P<0.05; **P<0.01.

Figure 5:
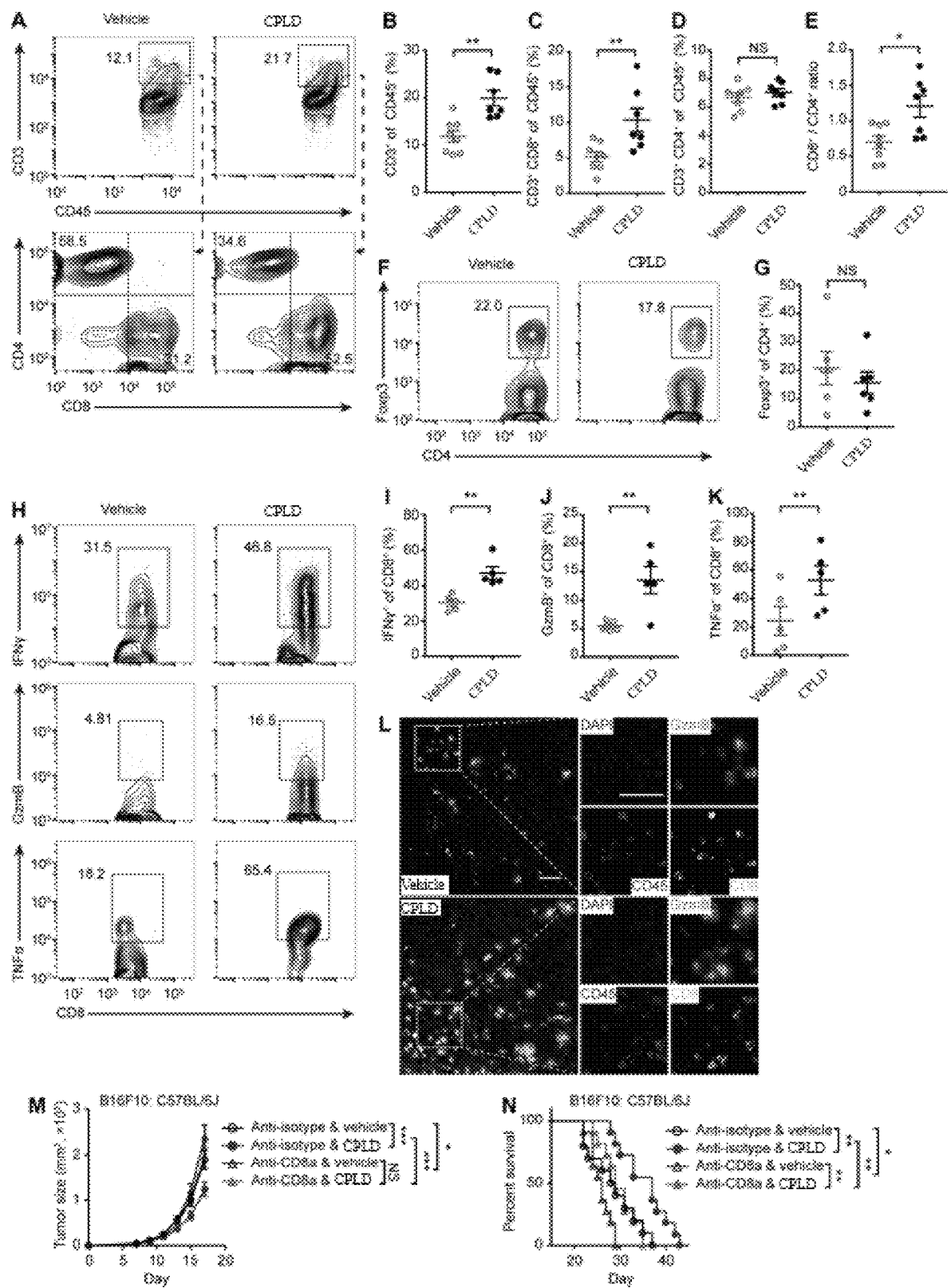
FIG. 5 shows a data graph that the CPLD improves and enhances the $CD8^+$ T cell function.

The test results of COLD are shown in FIG. 5. It is found that the CPLD treatment can significantly increase a proportion of CD8$^+$ T cells in the tumor, but has no significant effect on CD4$^+$ T cells (FIG. 5, A to E), as well as no effect on a proportion of Treg (F to G). Intracellular staining has showed that the CPLD can promote the function of CD8~ T cells and enhance the expression of IFNγ, Granzyme B and TNFα (H to K). Further immunofluorescence staining experiments also find that the CPLD can increase the proportion of CD8 T cells and promote the expression of Granzyme B (L). Further, mice were continuously injected with anti-CD8 antibodies to delete CD8+ T cells in the mice, to construct a melanoma model, followed by investigation of an anti-tumor activity of the compounds. The results show that the anti-tumor effect of CPLD is significantly reduced in the CD8$^+$ T cell-depleted tumor model and the nude mouse tumor model, confirming that the CPLD can further promote the function of CD8 T cells by regulating the function of TAMs to exert the anti-tumor activity (M to N).

Example 2

Preparation of Sulfates:
In the 28 substances prepared in Example 1, a 4% sulfuric acid ethanol solution was added to pH=4, followed by filtering and drying to obtain the sulfates.

Example 3

Preparation of Hydrochlorides:
In the 28 substances prepared in Example 1, a 4% hydrochloric acid ethanol solution was added to pH=4, followed by filtering and drying to obtain the hydrochlorides.

Example 4

Preparation of Phosphates:
In the 28 substances prepared in Example 1, a 4% phosphoric acid solution was added to pH=4, followed by filtering and drying to obtain the phosphates.

Example 5

Preparation of Tartrates:
In the 28 substances prepared in Example 1, a 4% tartaric acid solution was added to pH=4, followed by filtering and drying to obtain the tartrates.

Example 6

Preparation of Citrates:
In the 28 substances prepared in Example 1, a 4% citric acid solution was added to pH=4, followed by filtering and drying to obtain the citrates.

Example 7

Preparation of Formates:
In the 28 substances prepared in Example 1, a 4% formic acid solution was added to pH=4, followed by filtering and drying to obtain the formates.

Example 8

Preparation of Oxalates:
In the 28 substances prepared in Example 1, a 4% oxalic acid solution was added to pH=4, followed by filtering and drying to obtain the oxalates.

Example 9

Preparation of Injections:
The salts prepared in Examples 2-8 were added with water for injection, and finely filtered, potted and sterilized to obtain the injections.

Example 10

Preparation of Powder Injections:
The salts prepared in Examples 2-8 were dissolved in sterile water for injection, stirred until dissolved, filtered with a sterile suction filtration funnel, fine-filtered in a sterile manner, packaged in ampoules, freeze-dried at a low temperature and aseptically sealed to obtain the powder injections.

Example 11

Preparation of Powders:
With a mass ratio of 9:1, the salts prepared by Examples 2-8 were mixed with an excipient to obtain the powders Example 12

Preparation of tablets.
In a mass ratio of 1:(5-10), the salts prepared in Examples 2-8 were mixed with an excipient, and tabletted to obtain the tablets.

Example 13

With a mass ratio of 5:1, the salts prepared in Examples 2-8 were mixed with an excipient to obtain capsules, granules or dissolved medicines.

Example 14

With a mass ratio of 3:1, the salts prepared in Examples 2-8 were mixed with an excipient to obtain capsules, granules or dissolved medicines.

The above descriptions are merely preferred implementations of the present disclosure. It should be noted that a person of ordinary skill in the art may further make several improvements and modifications without departing from the principle of the present disclosure, but such improvements and modifications should be deemed as falling within the protection scope of the present disclosure.

What is claimed is:

1. A furan-aspidospermine dimer or a pharmaceutically acceptable salt thereof, having a following structure formula I-1

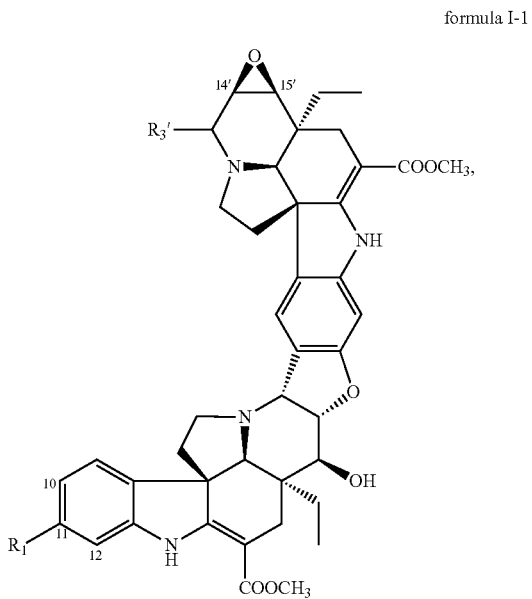

wherein, $R_1$ is H, and $R_3'$ is H;
wherein the furan-aspidospermine dimer is prepared by a process comprising the following steps:

crushing and soaking dried stems and leaves (14 kg) of *Melodinus tenuicaudatus* in 95% ethanol for 3 times for 24 h each time; combining resulting extracts, distilling off a solvent under reduced pressure, and suspending a resulting crude extract in water;

adjusting a pH value of the crude extract to 2 to 3 by adding 1% aqueous hydrochloric acid, stirring, and extracting with EtOAc; adjusting a pH value of a resulting aqueous layer to 9 to 10 with a 10% aqueous ammonia solution, and then extracting with the EtOAc to obtain 17 g of a total alkaloid extract;

subjecting the total alkaloid extract to silica gel column chromatography and chloroform-methanol gradient elution, and combining resulting approximate fractions to obtain 5 fractions;

subjecting a 4th fraction (2 g) to the silica gel column chromatography, elution with chloroform-methanol (15:1 to 8:1), and then silica gel atmospheric-pressure and medium-pressure column chromatography; repeatedly purifying a resulting product by elution systems such as petroleum ether/acetone (4:1), petroleum ether/ethyl acetate (3:1), chloroform/acetone (9:1) and methanol/water (60% to 80%), to obtain a compound melodinine K; and mixing the resulting melodinine K, chloroform, perchloric acid and m-chloroperoxybenzoic acid, followed by conducting oxidation reaction under 0° C. to obtain the furan-aspidospermine dimer.

2. A pharmaceutical composition, comprising the furan-aspidospermine dimer or the pharmaceutically acceptable salt thereof according to claim 1 and a pharmaceutically acceptable carrier.

3. The pharmaceutical composition according to claim 2, wherein the furan-aspidospermine dimer or the pharmaceutically acceptable salt thereof has a mass percentage content of greater than or equal to 10% in the pharmaceutical composition.

* * * * *

UNITED STATES PATENT AND TRADEMARK OFFICE
CERTIFICATE OF CORRECTION

PATENT NO. : 12,171,835 B2  
APPLICATION NO. : 17/693329  
DATED : December 24, 2024  
INVENTOR(S) : Xianghai Cai et al.

It is certified that error appears in the above-identified patent and that said Letters Patent is hereby corrected as shown below:

On the Title Page

Item (73) Assignees, delete "Kunming Institute of Botany, Kunming (CN); Chinese Adacemy of Sciences, Beijing (CN)" and insert -- Kunming Institute of Botany, Chinese Academy of Sciences, Kunming City (CN) --

Signed and Sealed this  
Fourth Day of February, 2025

Coke Morgan Stewart  
*Acting Director of the United States Patent and Trademark Office*